United States Patent
Higashida et al.

(10) Patent No.: US 6,954,700 B2
(45) Date of Patent: Oct. 11, 2005

(54) EFFICACY OF BIOLOGICAL STATE AND ACTION AFFECTING BIOLOGICAL STATE, JUDGING APPARATUS, JUDGING SYSTEM, JUDGING PROGRAM AND RECORDING MEDIUM HOLDING THE PROGRAM

(75) Inventors: Gesshi Higashida, Fukuoka (JP); Toshiyuki Shimizu, Fukuoka (JP); Tiejun Miao, Yokohama (JP); Wasei Miyazaki, Tokushima (JP); Hideyuki Asaoka, Takasaki (JP)

(73) Assignees: Computer Convenience Inc., Fukuoka (JP); Bio-Complex System Research Institute, Itano-gun (JP)

( * ) Notice: Subject to any disclaimer, the term of this patent is extended or adjusted under 35 U.S.C. 154(b) by 20 days.

(21) Appl. No.: 10/474,507

(22) PCT Filed: Apr. 25, 2002

(86) PCT No.: PCT/JP02/04114
§ 371 (c)(1),
(2), (4) Date: Oct. 21, 2003

(87) PCT Pub. No.: WO02/087434
PCT Pub. Date: Nov. 7, 2002

(65) Prior Publication Data
US 2004/0137639 A1 Jul. 15, 2004

(30) Foreign Application Priority Data
Apr. 25, 2001 (JP) ........................ 2001-128011

(51) Int. Cl.[7] .................. G06F 19/00; G06F 15/18
(52) U.S. Cl. .................. 702/19; 600/300; 706/924
(58) Field of Search .................. 702/19; 600/300, 600/301, 481, 485, 508, 509, 515, 529, 544, 518, 519; 607/2, 5; 706/924, 20, 22

(56) References Cited

U.S. PATENT DOCUMENTS

| | | | | | |
|---|---|---|---|---|---|
| 5,626,627 | A | * | 5/1997 | Krystal et al. | 607/45 |
| 5,643,325 | A | * | 7/1997 | Karagueuzian et al. | 607/8 |
| 5,678,561 | A | * | 10/1997 | Karagueuzian et al. | 600/443 |
| 5,709,214 | A | * | 1/1998 | Skinner | 600/300 |
| 5,720,294 | A | * | 2/1998 | Skinner | 600/300 |
| 5,743,860 | A | * | 4/1998 | Hively et al. | 600/544 |
| 5,769,793 | A | * | 6/1998 | Pincus et al. | 600/515 |
| 5,846,189 | A | * | 12/1998 | Pincus | 600/301 |
| 5,857,978 | A | * | 1/1999 | Hively et al. | 600/544 |
| 6,021,345 | A | * | 2/2000 | Karagueuzian et al. | 600/518 |

(Continued)

FOREIGN PATENT DOCUMENTS

JP    10-314427    12/1998

OTHER PUBLICATIONS

Kaplan et al., "Chaotic Statistics of Biomedical Time Series", IEEE, 1991.*

Meng et al., "A comprehensive Nonlinear Analysis of Electromyogram", IEEE, 2001.*

(Continued)

Primary Examiner—Patrick J. Assouad
(74) Attorney, Agent, or Firm—Armstrong, Kratz, Quintos, Hanson & Brooks, LLP

(57) ABSTRACT

A method of judging a biological state comprising using: (1) correlation and/or symmetry between Lyapunov exponent and entropy; and/or (2) Higuchi fractal dimension, wherein the Lyapunov exponent, entropy and Higuchi fractal dimension are indices that can express chaotic nature and derived from time series data of biological signals from a subject.

20 Claims, 24 Drawing Sheets

U.S. PATENT DOCUMENTS

| | | | | |
|---|---|---|---|---|
| 6,094,593 | A | * | 7/2000 | Karagueuzian et al. ...... 600/518 |
| 6,422,998 | B1 | * | 7/2002 | Vo-Dinh et al. ............. 600/300 |
| 6,438,419 | B1 | * | 8/2002 | Callaway et al. ............... 607/5 |
| 6,594,524 | B2 | * | 7/2003 | Esteller et al. ................ 607/45 |
| 6,647,293 | B2 | * | 11/2003 | Meyer ............................ 607/5 |
| 6,835,176 | B2 | * | 12/2004 | McNair ...................... 600/300 |
| 2002/0087197 | A1 | * | 7/2002 | Meyer ............................ 607/5 |
| 2002/0103512 | A1 | * | 8/2002 | Echauz et al. ................. 607/9 |
| 2002/0156392 | A1 | * | 10/2002 | Arai et al. ................... 600/546 |
| 2003/0158587 | A1 | * | 8/2003 | Esteller et al ................ 607/45 |
| 2003/0163057 | A1 | * | 8/2003 | Flick et al. ................. 600/509 |
| 2004/0098061 | A1 | * | 5/2004 | Armoundas et al. .......... 607/17 |
| 2004/0107105 | A1 | * | 6/2004 | Shomi et al. ............... 704/270 |
| 2004/0137639 | A1 | * | 7/2004 | Miyazaki et al. ........... 436/181 |
| 2004/0176697 | A1 | * | 9/2004 | Kappenberger et al. .... 600/518 |
| 2004/0225201 | A1 | * | 11/2004 | McNair ...................... 600/300 |

OTHER PUBLICATIONS

He et al., "Measure the Structure in Heart Rate Variability", IEEE, 2000.*

Iwase et al., "Chaotic Features of Rhythmic Joint Movement", IEEE, 2001.*

Signorini et al., "Complex Dynamics Assessment in 24–Hour Heart Rate Variability Signals in Normal and Pathological Subjects", IEEE, 1993.*

Uzun et al., "Nonlinear Analysis of Heart Rate Variability", IEEE, 2001.*

Hoyer et al., "Nonlinear Analysis of Heart Rate and Respiratory Dynamics", IEEE, 1997.*

Owis et al., "Robust Feature Extraction From ECG Signals Based on Nonlinear Dynamical Modeling", IEEE, 2001.*

Positano et al., "Nonlinear Analysis of Carotid Artery Echographic Images", IEEE, Nov. 2000.*

Beckers et al., "Nonlinear Dynamics in Heart Rate Variability", IEEE, 2000.*

Radhakrishnan et al., "Estimating Regularlity in Epileptic Seizure Time–Series Data", IEEE, 1998.*

Albert Goldbeter, "Biochemical Oscillations and Cellular Rhythms—The molecular basis of Periodic and Chaotic behavior", Cambridge University Press, (1996), table of contents and pp. 20–21, 78–79, 120–121 and 386–387.

Weiming Yang, A.J. Mandell et al.; Physical Review E, vol. 51, No. 1, pp. 102–110.

Ichiro Tuda, Takashi Tahara, "Chaotic Pulsation in Human Capillary Vessels and its Dependence on Mental and Physical Conditions", International Journal of Bifurcation and Chaos, vol. 2, No. 2, (1992), pp. 313–324.

Takeo Sumida et al.; Mental Conditions Relected by the Chaos of Pulsation in Capillary Vessels, ibid, vol. 10, No. 9, (2000), pp. 2245–2255.

Takashi Tahara, "The study of practical application of Chaos in clinical medicine", Journal of Society of Biomechanisms Japan, vol. 19, No. 2, (1995) pp. 105–116 (with abstract).

* cited by examiner

FIG. 14
Correlation between Entropy and Lyapunov exponent
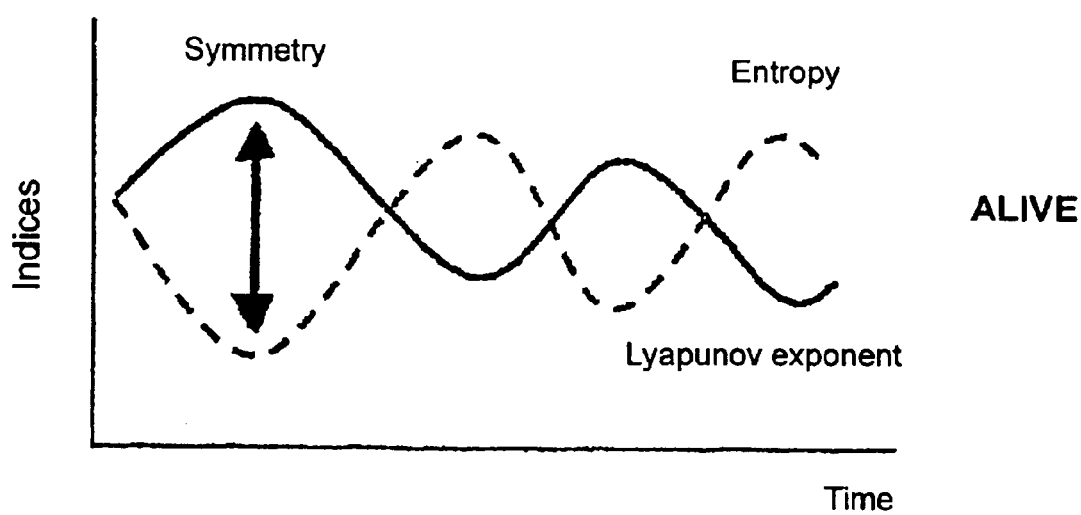
ALIVE
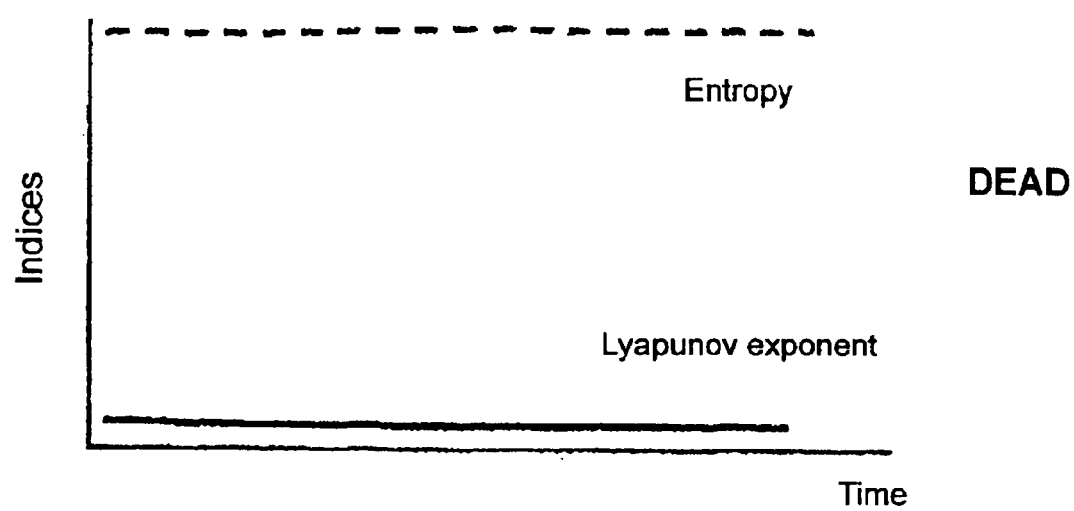
DEAD Left figs: left hand, Right figs: right hand,
Upper figs: looking at picture (H), Lower figs: calculating (K)

EFFICACY OF BIOLOGICAL STATE AND ACTION AFFECTING BIOLOGICAL STATE, JUDGING APPARATUS, JUDGING SYSTEM, JUDGING PROGRAM AND RECORDING MEDIUM HOLDING THE PROGRAM

TECHNICAL FIELD

The present invention relates to a judging method, a judging apparatus, a judging system, a judging program for a biological state, and a recording medium holding the program. In this specification, the maximum Lyapunov exponent (λ1) may be simply referred to as Lyapunov exponent.

BACKGROUND ART

It is well known that the dynamic behavior of the glycolysis system or enzymes, intracellular cAMP, movement of calcium ion and the like in a living body show chaotic oscillation caused by the energy in non-equilibrium, feedbacks in a signal transduction system and the interference called crosstalk (Albert Goldbetter, Biochemical Oscillations and Cellular Rhythms—The Molecular Basis of Periodic and Chaotic Behavior, Cambridge University Press). This oscillating system in non-equilibrium containing fluctuation means life itself, and the adaptability of life is measured from the chaotic fluctuation (Weiming Yang, A. J. Mandell et al. Physical Review E.; 1995, Vol.51, No.1: 102–110).

The following items are known to show different chaotic fluctuation in a healthy (normal) state and in an abnormal state such as morbidity (W. Yang, the same as the above).

1) Fluctuation in change of cell number with time under hematological disorders
2) Change in behavior patterns of animals or existence patterns of intracerebral enzymes or intracerebral receptors at the time of drug stimulation
3) Patterns of heartbeat intervals under various cardiac disorders
4) Change of the duration of desensitization when a response among various kinds of biological responses to stimuli is desensitized by a certain stimulus
5) Experimental epilepsy
6) Hormonal secretion patterns when neuroendocrine cells mutate into carcinoma
7) Electrocardiographic patterns useful for prediction of the rejection of a heart transplant
8) Brain wave patterns under disease of neurodegenerative disorders
9) Neuroendocrine patterns, electrocardiogram, brain waves accompanying aging
10) Electrocardiographic patterns at the time of imminent ventricular fibrillation.

Thus, many pathophysiological examples are known where loss of chaotic fluctuation is considered as one of the causes of morbidity. Without mentioning the formulation by Ilya Prigogine, many other people point out that the principle underlying the existence of life is based on the integration of oscillations including fluctuations, called self-organization. This is supported by the data on pharmaceutical drugs relating to nerve-hormone-immune system. Therefore, it is not surprising even if the relation between loss of fluctuation and morbidity is observed in almost all life processes. The nerve-hormone-immune system, heartbeat and the like preserve their soundness by holding the chaotic fluctuation. Maintenance of chaotic nature also leads to the treatment and the prevention of mind, nerve or immune related diseases or periodic idiopathy. The clinical effect and the result of basic animal experiments by these drugs are considered ascribable to such amelioration.

In the field of brain or nerve related diseases, the advances in chaos measurements and analysis methods for brain waves or finger pulses have revealed that for example, the overall picture of non-linearity of neural system can be grasped as an overall picture in which the macroscopic state of the system dramatically and diversely changes with ion concentrations in neurocytes, membrane potential, synaptic currents, synaptic connection strength, newly produced synaptic connections, various substances to make the environment of a neural system, input signals, etc (Kazuyuki Aihara, Chaos in Neural System, Tokyo Denki University Press).

The finger pulse is used as one of the indices of total condition of a living body by the following method. The variation of blood flowing through capillary vessels of a fingertip is measured using an infrared sensor, for example, for one minute, the resulting waveform of two-dimensional electric signal is mathematically transformed to a four-dimensional attractor, and then the chaos analysis thereof is performed. A finger pulse is considered to consist of at least three pulse wave components: heartbeat, respiration, and action of hormone on the vascular wall. These oscillating components each having a different fundamental frequency are integrated and expressed as finger pulse chaos (Kunihiko Kaneko and Ichiro Tsuda, Chaotic Scenario of The Complex System, Asakura Publishing).

Therefore, biological information expressed by the pulse wave chaos reflects the total of interactions among a central nervous system, peripheral circulation system and metabolic system. For this reason, the pulse wave chaos reflects a mental condition better than the chaos observed with electrocardiogram. The chaos analysis of finger pulse and its clinical application are explained in detail in papers by Tsuda, Tahara and so on (Ichiro Tsuda and Takashi Tahara, Chaotic Pulsation in Human Capillary Vessels and Its Dependence on Mental and Physical Conditions, International Journal of Bifurcation and Chaos; 1992, Vol.2, No.2: 313–324/Takeo Sumida et al. Mental Conditions Reflected by the Chaos of Pulsation in Capillary Vessels, International Journal of Bifurcation and Chaos; 2000, Vol.10, No.9: 2245–2255/Takashi Tahara, Clinical application of chaos, Society of Biomechanisms; 1995, Vol.19, No.2: 105–116).

It is stated in these papers that the deterministic chaos contained in a finger pulse is substantially the same as the chaos also observed in brain wave or electrocardiogram and is related to mentality, state of mind, illness, and maturity of human being. The clinical symptom of a neurotic or depressive patient is parallel to the trend of Lyapunov exponents (λ1, λ2) that are indices of chaotic nature. As the symptom improves, λ1 increases and λ2 decreases. The structure of an attractor also changes with the improvement of a disease from a weak and simple structure to a strong and complicated structure.

The above-described facts suggested that Lyapunov exponent can be one index of the self-organization ability or soundness of a living body. However, Lyapunov exponent as an index of chaotic nature originally expresses the magnitude of the time aperiodicity of a system. If the system shows chaotic nature, fractal changes of such index with time is considered natural. This is also supported by our data. The degree of soundness of a system can be estimated by the exclusive measurement of the index alone only after repeating the measurement at a different interval over a long term. Therefore, such index has been of quite limited use in the field of clinical diagnosis.

An object of the present invention is to provide a judging method for a biological state and a method of judging how a biological state is influenced by a certain action.

An object of the present invention is to provide a judging apparatus, a judging system, a judging program for performing such judging method, and a recording medium holding the program.

DISCLOSURE OF THE INVENTION

In view of the above problem, the present inventors carried out intensive research to achieve the judging method for a biological state accurately. As a result, it was found that a good or normal biological state and the case where some part of mentality or body is not good or not normal (including illness) can be easily judged by the following methods: calculating the average values of Lyapunov exponents and entropies per every definite period of time from time series data of a biological signal such as pulse wave and conducting the symmetry analysis of these two data using M-Symmetry method, Wavelet Transformation and a method base on Mirror Value; and/or performing Bernoulli shift to calculate time series data of Lyapunov exponents and entropies from the same biological signal and determining the correlation therebetween.

In addition, it was found that judgement accuracy can be remarkably improved by analyzing time series data of a biological signal by means of F-symmetry method to determine a ratio of Higuchi Fractal dimensions (D1/D2) and further combining symmetry analysis using the ratio.

Moreover, it was found that the efficacy of an action that may influence a biological state can be determined by judging a biological state before and after taking the action.

The present invention provides the following judging method, judging apparatus, judging system, judging program for a biological state, and recording medium holding the program.

(1) A method of judging a biological state comprising using:
 correlation and/or symmetry between Lyapunov exponent and entropy; and/or
 Higuchi fractal dimension,
wherein the Lyapunov exponent, entropy and Higuchi fractal dimension are indices that can express chaotic nature derived from time series data of biological signals from a subject.

(2) The method according to the item (1) comprising:
 the step of analyzing the correlation and/or the symmetry between the Lyapunov exponent and the entropy derived from time series data of biological signals from a subject; and
 the step of judging the biological state based on the result of analyzing the correlation and/or symmetry.

(3) The method according to the item (1), wherein the correlation between the Lyapunov exponent and the entropy is analyzed using DFA method (Detrended Fluctuation Analysis).

(4) The method according to the item (1), wherein the DFA method comprising the step of performing microscopic DFA analysis and the step of performing macroscopic DFA analysis.

(5). The method according to the item (1), wherein the correlation between the Lyapunov exponent and the entropy is analyzed using any method selected from the group consisting of M-symmetry method, Wavelet analysis method and a method based on Mirror value.

(6). The method according to the item (1) comprising the steps of:
 calculating two or more Lyapunov exponents and two or more entropies from time series data of biological signals from a subject and determining the maximum values among the Lyapunov exponents as a maximum Lyapunov exponents;
 determining offset values (Os) corresponding to the maximum Lyapunov exponents and the entropies;
 calculating Mirror values from the maximum Lyapunov exponents and the entropies; and
 calculating weighted Lyapunov exponents from the Mirror values and the offset values.

(7) The method according to the item (1) comprising using a ratio of two Higuchi fractal dimensions (D1/D2) and/or a F-constant as the Higuchi fractal dimension.

(8) The method according to the item (1) further comprising the step of calculating a ratio of Higuchi fractal dimensions (D1/D2) by analyzing time series data of biological signal from a subject using F-symmetry method, wherein the biological state is judged based on the correlation and/or the symmetry between Lyapunov exponent and entropy and on the ratio of Higuchi fractal dimensions (D1/D2).

(9) The method according to the item (1), wherein the time series data of biological signal are obtained from a pulse wave.

(10) The method according to the item (1), wherein the biological state is a mental or physical state of a morbid or non-morbid subject.

(11) A method of judging efficacy of an action that may affect a biological state comprising the steps of:
 judging the biological state at a certain point of time according to the method of the item (1);
 taking the action that may change the biological state;
 analyzing time series data of biological signal after the action to determine correlation and/or symmetry between Lyapunov exponent and entropy; and
 comparing the correlation and/or the symmetry between Lyapunov exponent and entropy before the action with the correlation and/or the symmetry between Lyapunov exponent and entropy after the action to judge whether an influence of the action on a living body is positive, negative or neutral (unchanging).

(12) The method according to the item (11), wherein the action is selected from the group consisting of preventive or therapeutic actions on diseases such as medication, dialysis, use of medical appliances (e.g., radiation or laser irradiation, treatment by electric or magnetic pulse, rehabilitation and the like), ingestion of food that may ameliorate a biological state, and producing a physical or mental stimulus.

(13) The method according to the item (1) comprising the steps of:
 calculating two or more Lyapunov exponents and two or more entropies from time series data of biological signals from a subject and determining the maximum values among the Lyapunov exponents as maximum Lyapunov exponents; and
 calculating scaling coefficients and wavelet coefficients from the maximum Lyapunov exponents and the entropies.

(14) The method according to the item (1) or (7) comprising judging a calculation result of time series data of biological signals from the subject using an Artificial Neural Network.

(15) An apparatus for judging a biological state based on time series data of biological signals from a subject comprising a processing unit and a detection unit,
wherein the processing unit controls the detection unit to collect the time series data, calculates correlation and/or symmetry between a Lyapunov exponent and an entropy as indices that can express chaotic nature and/or Higuchi fractal dimension from the time series data, and uses the calculation result to perform the judgement.

(16) A system for judging a biological state comprising a measuring apparatus to collect time series data of biological signals from a subject and a judging apparatus for judging the biological state based on the time series data,
wherein the measuring apparatus transmits the time series data via a communication line; and
the judging apparatus calculates from the transmitted time series data correlation and/or symmetry between a Lyapunov exponent and an entropy and/or Higuchi fractal dimension as indices that can express chaotic nature, and uses the calculation result to perform a judgement.

(17) A system for judging a biological state comprising a measuring apparatus to collect time series data of biological signals from a subject and a judging apparatus for judging the biological state based on the time series data,
wherein the measuring apparatus calculates from the transmitted time series data correlation and/or symmetry between a Lyapunov exponent and an entropy and/or Higuchi fractal dimension as indices that can express chaotic nature and transmits the calculation result via a communication line; and
the judging apparatus uses the calculation result to perform a judgement.

(18) The system for judging according to the item (16) or (17), wherein the judging apparatus transmits a result of the judgement to the measuring apparatus.

(19) A program for judging a biological state comprised in an apparatus for judging a biological state of a subject based on time series data of biological signals from the subject,
wherein a function of calculating correlation and/or symmetry between Lyapunov exponent and entropy and/or Higuchi fractal dimension as indices that can express chaotic nature from the time series data is fulfilled by the apparatus.

(20) The program according to the item (19) further fulfilling the functions of:
determining maximum values among the two or more Lyapunov exponents as maximum Lyapunov exponents;
determining offset values corresponding to the maximum Lyapunov exponents and the entropies;
calculating Mirror values from the maximum Lyapunov exponents and the entropies; and
calculating weighted Lyapunov exponents from the Mirror values and the offset values.

(21) The program according to the item (19) further fulfilling the functions of:
determining maximum values among the two or more Lyapunov exponents as maximum Lyapunov exponents; and
calculating scaling coefficients and wavelet coefficients from the maximum Lyapunov exponents and the entropies.

(22) The program according to the item (19) further fulfilling the function of performing macroscopic DFA method and microscopic DFA method with respect to the Lyapunov exponent and the entropy.

(23) The program for judging a biological state according to the item (19) fulfilling the function of calculating Higuchi fractal dimension and F-constant from the time series data.

(24) A computer-readable recording medium holding the judging program according to any one of the items (19) to (23).

BRIEF DESCRIPTION OF DRAWINGS

FIG. 14 shows conceptual diagrams showing the correlation between both of entropy and Lyapunov exponent and a state of life or death.

As shown in FIG. 10, the critical point showing the effect of medication is observed at the arrow.

In FIG. 25, ♦ indicates entropy and ● Lyapunov exponent. The horizontal axis indicates a measurement date and the vertical axis indicates entropy (3 to 7) and Lyapunov exponent (−4 to 12).

In FIG. 26, ▲ indicates entropy and ♦ Lyapunov exponent. The horizontal axis indicates a measurement date and the vertical axis indicates entropy (3.5 to 7.5) and Lyapunov exponent (−2.0 to 12.0).

In FIG. 27, ♦ indicates entropy and ● Lyapunov exponent.

BEST MODE FOR CARRYING OUT THE INVENTION

Figure 1:
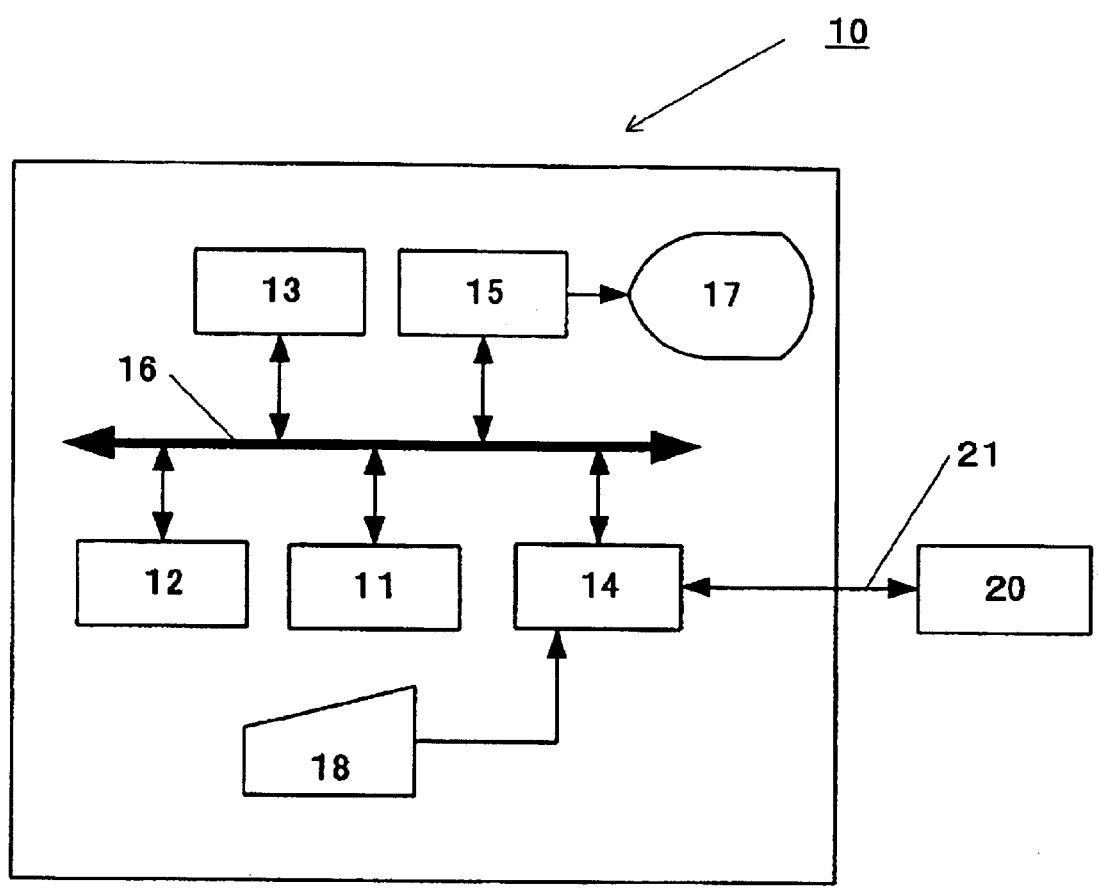
FIG. 1 is a block diagram showing a schematic construction of the apparatus for judging a biological state according to the first embodiment of the present invention.

The best mode for carrying out the present invention is described below referring to the Figures.

Lyapunov exponents which indicate chaotic nature exist in large numbers, and among them the maximum Lyapunov exponent ($\lambda 1$) is used herein. The first Wolf Lyapunov exponent ($\lambda 1$) will be hereinafter simply indicated as Lyapunov exponent. In addition, Lyapunov exponent means the maximum Lyapunov exponent unless otherwise specified.

Lyapunov exponent and entropy can be derived from the time series data of chaotic and fluctuating biological signals, such as pulse waves, electrocardiogram, brain waves, heart rate and the like. Although a pulse wave is especially preferred as a biological signal, the other biological signals can be also used.

The pulse wave is preferably a finger pulse measured from a fingertip, however, it may be measured from the other surface of a living body (an earlobe, a palm, the base part of a finger (ring position)).

As an apparatus for measuring pulse wave, the pulse wave collection system (Bacs detector) from Computer Convenience Inc. can be used. The calculation of Lyapunov exponent and entropy from a pulse wave will be described later. A Lyapunov exponent is calculable for example according to the disclosure of the specification of Japanese Patent number No. 1891534 (Japanese Unexamined Patent Publication No. 1992-208136). An entropy from a pulse wave is calculable according to a well-known method (Ichiro Tuda, Takashi Tahara, Chaotic Pulsation in Human Capillary Vessels and Its Dependence on Mental and Physical Conditions, International Journal of Bifurcation and Chaos.; 1992, Vol.2, No.2: 313–324).

In one preferable embodiment, the measurement of the time series data of biological signals, such as a pulse wave, can be performed usually for one minute or more, preferably for about 3 to 30 minutes, successively or in 2 to 18 times. One consecutive measuring time may be preferably one minute or more, and especially about 2 to 5 minutes. It is especially preferred that a one minute-measurement is repeated for three times as a set and the three sets of data are measured and analyzed.

While a human subject is mainly targeted for the judging method of the present invention, a mammal, such as a cow, horse, dog, cat, pig, mouse, rat, guinea pig, rabbit and the like can be also used as the subject.

According to the present judging method using Lyapunov exponent and entropy, for example in the case of determining whether a certain human subject belongs to the first biological state or the second biological state, a judging criterion is fixed beforehand on the basis of Lyapunov exponents and entropies as to the subjects each belonging to the first or the second biological state, then the Lyapunov exponent and the entropy of each subject are analyzed to determine whether the biological state is the first or second state in accordance with the judging criterion. When n biological states (n is three or more) are used in judging, judging criteria are fixed beforehand as to the first to nth biological states and the judgement is made similarly. The judgement can also be made when Higuchi fractal dimension is used in place of Lyapunov exponent or entropy.

As biological states for judgement, normal and abnormal (e.g. disease) states can be used. For example, in the case where a subject is known in the mental condition of either depression or schizophrenia, it is also possible to judge under the condition: depression as the first biological state and schizophrenia as the second.

For accurate judgement, the number of the subjects in each biological state used for fixing a judging criterion is preferably high, and the initial number of subjects at the time of starting the judgement is for example five or more, preferably 10 or more, and more preferably 20 or more. The subjects are recorded after the judgement as basic data of each biological state, and consequently more accurate judgement can be attained by increasing the population of each biological state after a series of judgement. Especially as to mental condition and the like, when the criteria for judging normality and abnormality (e.g. depression) change or a new name is given to a disease, it is also possible to change the basic data of each biological state used for fixing a judging criterion.

In the present invention, the judging criterion of biological condition is based on the Lyapunov exponent and the entropy calculated from the data obtained from a subject in each biological state, and is preferably prepared based on the result of analyzing the symmetry and/or the correlation between the Lyapunov exponent and the entropy. M-symmetry method and Wavelet method are used as a method for analyzing the symmetry between Lyapunov exponent and entropy concerning a subject. DFA (Detrended Fluctuation Analysis) and an analyzing method using long range correlation may be used as an analytical method of correlation, and DFA may be preferably used. In addition, Higuchi fractal dimension is calculated from the measurement data of a subject in each biological state, from which an index F-constant is drawn to be used as another judging criterion in the present invention (F-symmetry method). In judging a biological state or an effectiveness of an action on a living body, these methods can be used singly or in combination of two or more.

Embodiment 1

Judging Apparatus for a Biological State

FIG. 1 is a block diagram showing a schematic construction of the judging apparatus for a biological state according to the first embodiment of the present invention. The judging apparatus for a biological state according to this embodiment comprises a main unit 10, a detecting unit 20 and a communication cable 21.

The main unit 10 is provided with a central processing unit 11 (hereafter referred to as CPU), a memory unit 12, a recording unit 13, an interface unit 14, a video unit 15, a data bus 16, a display unit 17 and an operating unit 18. The detection unit 20 has a probe equipped with a light emitting diode for emitting an infrared lights and a phototransistor for receiving an infrared lights in the frequency band emitted by the light emitting diode, and an A/D converter (neither is illustrated).

Each part inside the main unit 10 is controlled by CPU 11, and the control by this CPU 11 and the data transmission between each part are performed via the data bus 16. The CPU 11 receives the directions from the operating unit 18 via the interface unit 14.

The CPU 11 controls the light emitting diode and the A/D converter in the detection unit 20 via the interface unit 14. Under the control of CPU 11, the light emitting diode emits infrared lights and the A/D converter samples received signals of the phototransistor. CPU 11 acquires sampling data via the communication cable 21 and the interface unit 14, and records them in the recording unit 13. For example, variation in the state of blood flow at fingertip, i.e., finger pulse data, can be obtained by setting the probe to the fingertip of a human body, receiving the infrared lights after transmitting through the finger (or after reflecting inside the finger) by the phototransistor, and sampling the resulting signal at fixed time intervals.

The CPU 11 reads out data from the recording unit 13 to the memory unit 12, performs processing such as calculation described later, and records the result in the predetermined area of the recording unit 13. The CPU 11 writes image data in a video memory (not shown) of the video unit 15, and the written image data is converted by a video converter (not shown) of the video unit 15 into a video signal suitable for the display unit 17, and is transmitted to the display unit 17 and displayed thereon.

Symmetry Analysis between Lyapunov Exponent and Entropy (i) M-symmetry (Mirror value symmetry) Method As stated above, M-symmetry method is one of the methods for analyzing the symmetry property between Lyapunov exponent and entropy with respect to measured data. In a normal and healthy person, the Lyapunov exponent and entropy obtained from a time series signal of pulse wave move in the directions opposite to each other, maintaining the soundness of the system as a complex. M-symmetry method is an analytical method based on this idea, where the symmetry property of these two indices (Lyapunov exponent and entropy) are numerically expressed. The concrete procedure of data processing will be described later. In M-symmetry method, the Lyapunov exponent and the entropy showing high symmetry are regarded close to normal state, and the ones showing low symmetry are regarded far from normal state.

Figure 2:
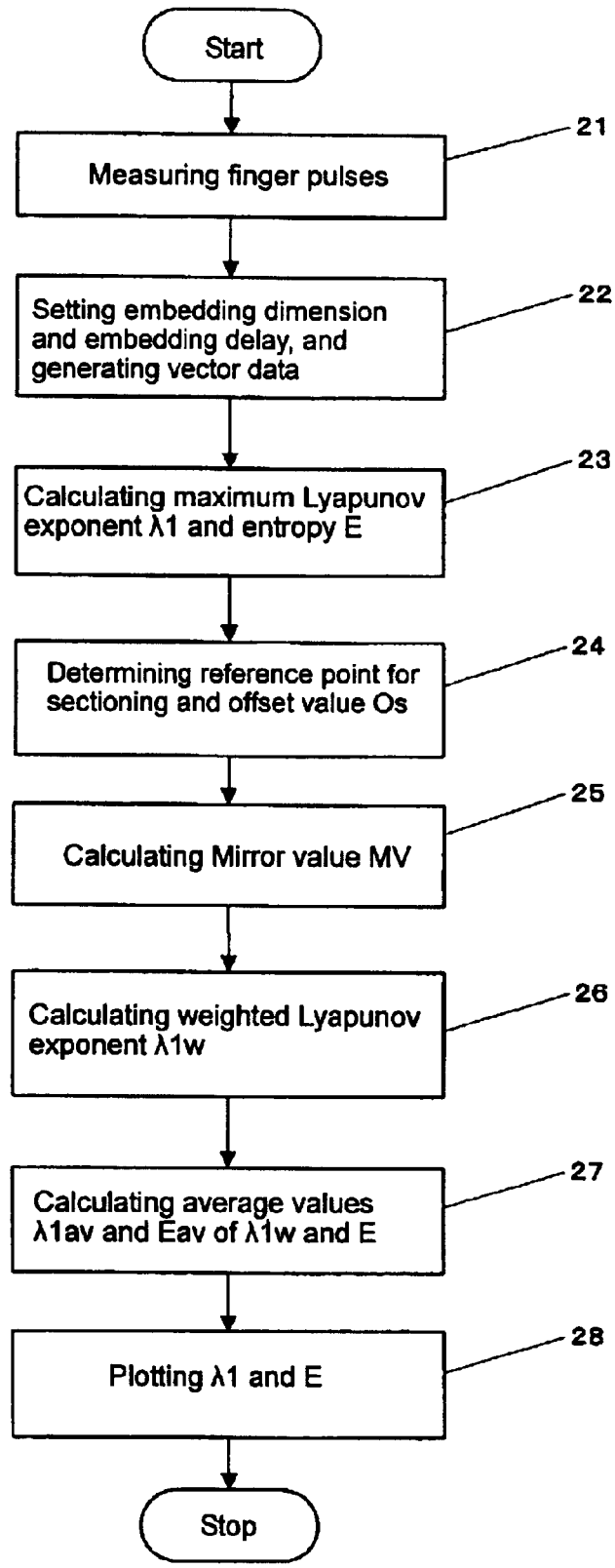
FIG. 2 is a flow chart illustrating the processing executed by CPU 11 in the judging method for a biological state using M-symmetry method performed in the apparatus for judging biological state shown in FIG. 1.

FIG. 2 is a flow chart illustrating the processing executed by CPU 11 in the judging method for a biological state using M-symmetry method performed in the judging apparatus for a biological state shown in FIG. 1. In each following step, calculation and like data processing are performed in the memory unit 12, and the result is recorded in the predetermined area of the recording unit 13 if necessary, for example when used at the following step.

First, in Step 21, finger pulses are measured from two or more subjects. As described above, the detection unit 20 is controlled to measure a finger pulse from each subject, and the obtained finger pulse data w(i,j;k) are recorded in the recording unit 13. Here, i represents the identification number uniquely assigned to each subject, j indicates the number of measurements, and k the sampling number given to each data in the order of sampling. A finger pulse data is obtainable under various kinds of measurement conditions. Hereinafter illustrated is the case where a sampling period is five milliseconds (msec) and a three-minute measurement is performed three times for each subject. Accordingly, three sets of time series data {w(i,j)} each consisting of 36000 data can be obtained from each subject i. Here, the brace { } is a symbol showing sampling data obtained in one three-minute measurement as time series data.

In Step 22, finger pulse data w(i,j;k) are read out from the recording unit 13, then an embedding dimension is set to four, an embedding delay τ to 10, and the four-dimensional vectors V(i,j;k) (k=1 to 36000) are generated from the data {w(i,j)} according to Formula 1.

$$V(i,j;k)=(W(i,j;k), W(i,j;k+\tau), W(i,j;k+2\tau), W(i,j;k+3\tau)) \quad \text{[Formula 1]}$$

In Step 23, maximum Lyapunov exponent λ1(i,j) and Entropy E(i,j) are calculated with respect to each (i,j) according to Formula 2 and Formula 3.

The maximum Lyapunov exponent λ1(i,j) is the largest one among four λ(i,j) calculated by Formula 2 with respect to each component of the four-dimensional vector V(i,j,k), i.e., w(i,j;k), w(i,j;k+τ), w(i,j;k+2τ), and w(i,j;k+3τ).

$$\lambda(i,\ j) = \lim_{N \to \infty} \frac{1}{N} \sum_{k=0}^{N-1} \log|f'(x_k)| \quad \text{[Formula 2]}$$

$$E(i,\ j) = -\sum_{k=1}^{N} P_k \log P_k \quad \text{[Formula 3]}$$

Here used for $\{x_k\}$ are time series data of w(i,j;k), w(i,j;k+τ), w(i,j;k+2τ) and w(i,j;k+3τ), components of four-dimensional vector V(i,j;k). In the dynamical system where the condition $x_{k+1}=f(x_k)$ are given using the predetermined function f, Lyapunov exponent λ(i,j) indicates how two trajectories $\{x_k\}$ starting from adjacent two points will separate from each other when n→∞.

$P_k$ represents the existence probability of data. Hence, the entropy E(i,j) is derived by the following: dividing the space containing four-dimensional vector V(i,j;k) into N pieces of small regions, expressing $P_k$ of each small region as the ratio of the number of data in each small region to the number of all data, and taking the sum of $P_k$ with respect to all the regions.

Figure 3:
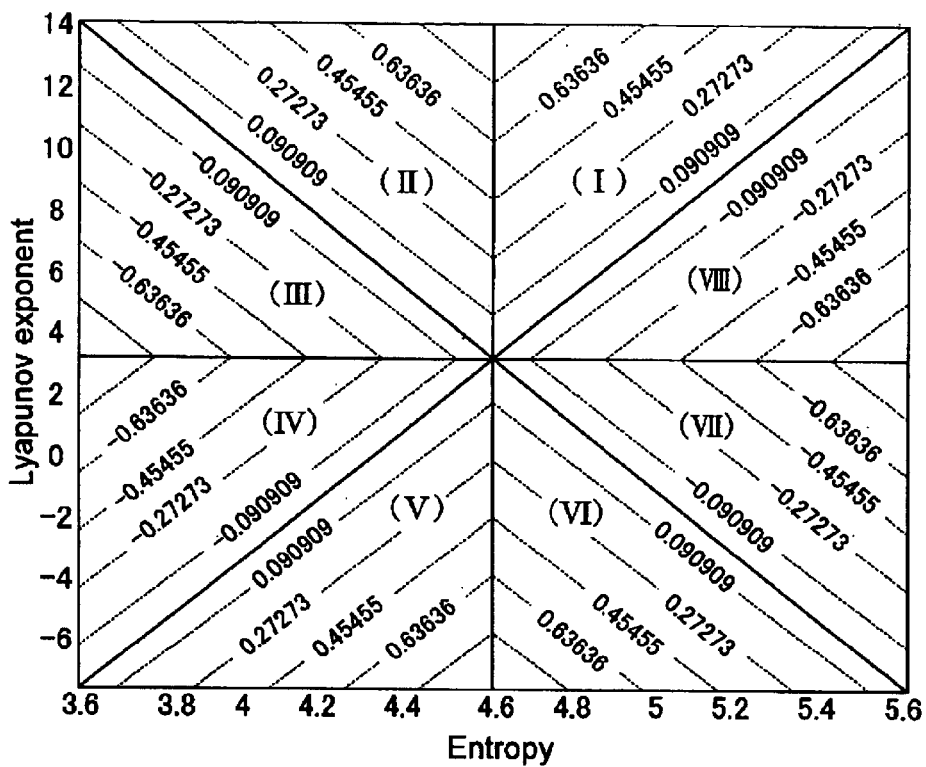
FIG. 3 is a Mirror symmetry diagram plotted in two-dimensional plane having axes of maximum Lyapunov exponent and entropy.

In Step 24, the entropy E(i,j) and the maximum Lyapunov exponent λ1(i,j) are plotted on a two-dimensional plane, the barycenter of the whole data is calculated, boundary lines through the barycenter are drawn at an angle of +45 or −45 with respect to the horizontal line, the two-dimensional plane (Mirror symmetry diagram) is sectioned into eight regions with reference to the predetermined point as indicated in FIG. 3, and the offset value (Os) is set to two as to regions I and II while one as to other regions.

In Step 25, Mirror Value MV(i,j) is calculated by Formula 4.

$$MV(i, j) = \frac{|\lambda 1(i, j)|}{\max|\lambda 1|} - \frac{|E(i, j)|}{\max|E|} \quad \text{[Formula 4]}$$

Here, max|λ1| and max|E| are maximum values of maximum Lyapunov exponent λ1(i,j) or entropy E(i,j), respectively, with respect to the measurement data of the whole group consisting of plural subjects. The analysis result of normality, DP (depression) and SP (schizophrenia) by Mirror Value is illustrated in FIG. 31.

In Step 26, in view of a region determined in Step 23 to which the maximum Lyapunov exponent λ1(i,j) and the entropy E(i,j) belong, a weighted Lyapunov exponent λ1w (i,j) is calculated by Formula 5 with respect to each (i,j).

$$\lambda 1w(i,j) = \lambda 1(i,j) \times (Os + MV(i,j)) \quad \text{[Formula 5]}$$

Os=2 when the maximum Lyapunov exponent λ1(i,j) and entropy E(i,j) belong to region I or II and otherwise Os=1, then a weighted Lyapunov exponent λ1w(i,j) is calculated by Formula 5.

In Step 27, average values λ1wav(i) and Eav(i) of weighted Lyapunov exponents λ1w(i,j) and entropies E(i,j) of the j-times measurements, respectively, are calculated.

In Step 28, each point indicating (i,j) is plotted on a graph with weighted Lyapunov exponent λ1w(i,j) on the vertical axis and E(i,j) horizontally, which will be transmitted to the video unit 15. The data transmitted to the video unit 15 is displayed on the display unit 17.

The average value of weighted Lyapunov exponents λ1wav(i) resulting from the above is compared to a reference value experimentally derived as to a population, enabling the judgement of the biological state of the subject i. In the method of calculating a reference value experimentally, pulse waves of normal (healthy) subjects are measured as many times as possible, the weighted Lyapunov exponents are calculated, and the average value thereof is treated as a reference value. If the average value λ1wav(i) of weighted Lyapunov exponents is larger than the reference value, the biological state is judged as being good.

Moreover, the biological state of the subject i can be judged also by comparing the plot figure prepared in Step 28 with a base line experimentally derived as to a population. As the method of calculating the reference value experimentally, pulse waves of normal (healthy) subjects are measured as many times as possible, the weighted Lyapunov exponents are calculated, and the average value thereof decides a base line.

Figure 4:
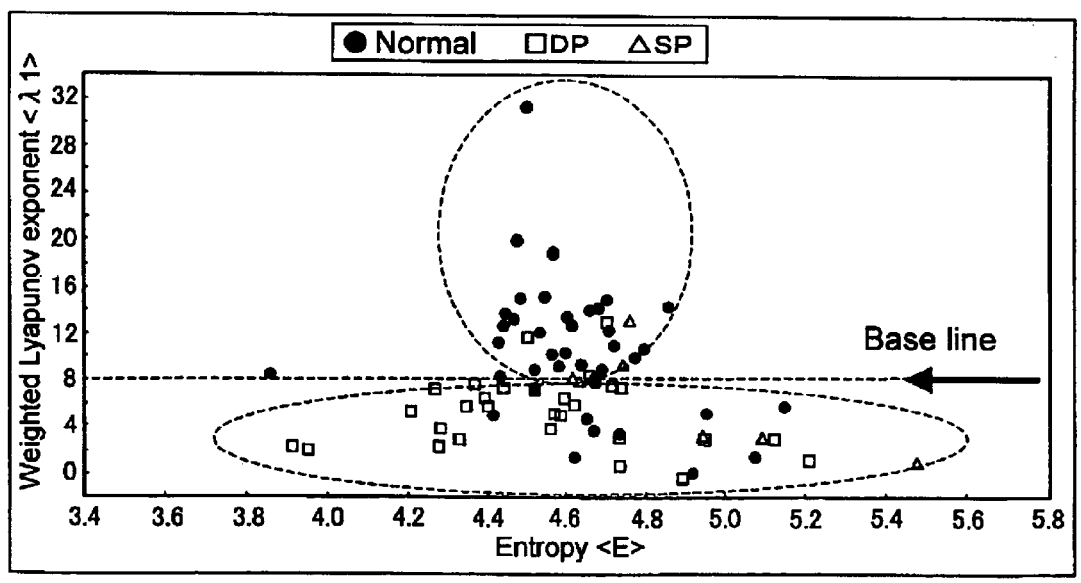
FIG. 4 illustrates an example of plotted figure obtained by Step 28.

FIG. 4 illustrates an example of the plot figure derived in Step 28. For example, the biological state of a subject is judged being normal when the plotted point is positioned above the horizontal base line, and abnormal when positioned below. In this example, the data of normal (Normal), depression (DP), and schizophrenia (SP) are plotted. Normals are distributed above the base line and DPs and SPs are below with a probability of 83%.

Embodiment 2
Symmetry Analysis Using Wavelet Transformation

Figure 5:
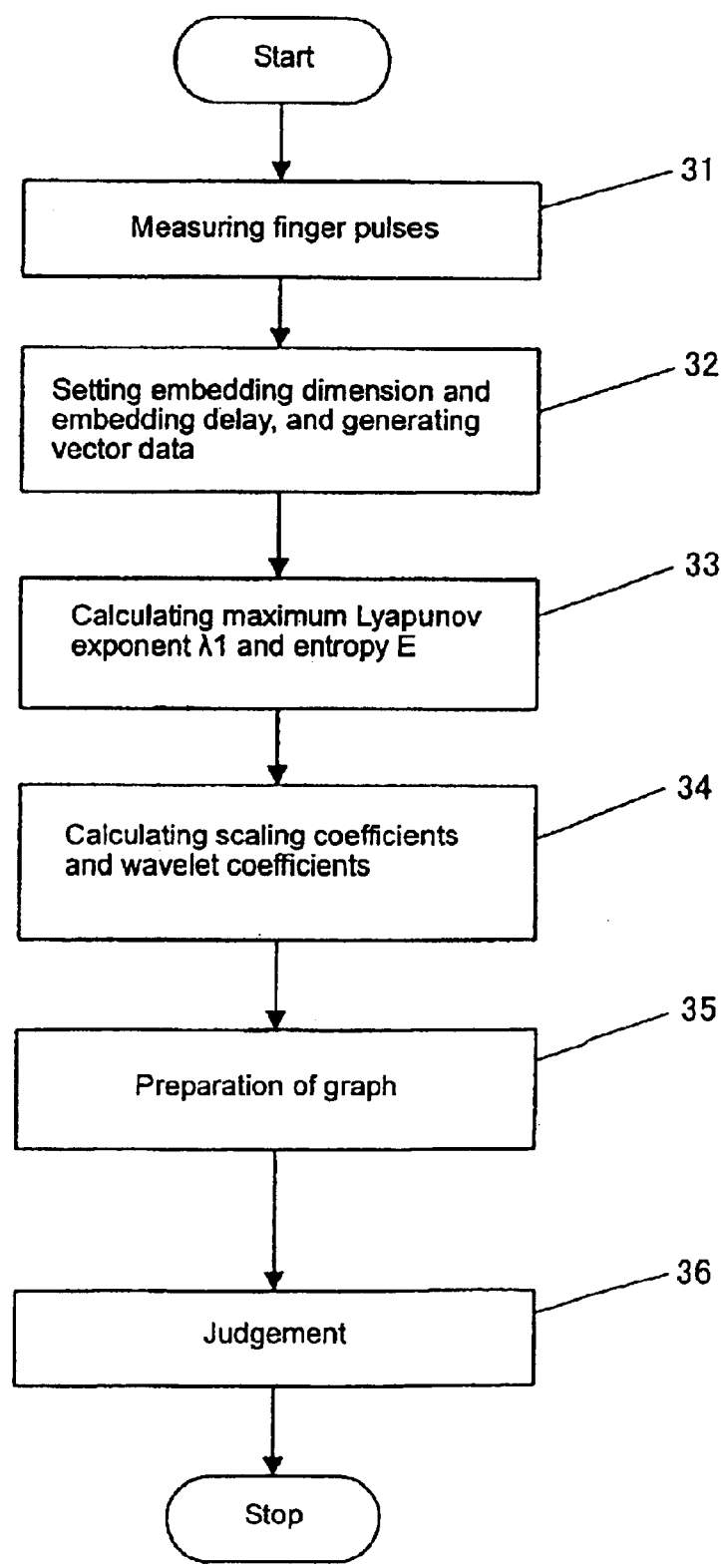
FIG. 5 is a flow chart showing the processing executed by CPU 11 in the judging method for a biological state using Wavelet Transformation performed in the apparatus for judging a biological state shown in FIG. 1.

As a method for analyzing the symmetry property between Lyapunov exponent and entropy of a subject, the method using Wavelet Transformation is described below. FIG. 5 is a flow chart showing the processing executed by CPU 11 in the judging method for a biological state using Wavelet Transformation performed in the apparatus for judging a biological state shown in FIG. 1.

In the same manner as in Step 21 of FIG. 2, finger pulse data are measured and recorded in the recording unit 13 in Step 31. Only measurements of a specific subject i is performed in this embodiment, where three times of a three-minute measurement are regarded as one set, and three or more sets of measurements are performed at regular time intervals. In the following, m (m≧3) represents a set number and the measurement data is expressed as w(i,m,j;k).

In Step 32, in the same manner as in Step 22 of FIG. 2, an embedding dimension is set to 4, an embedding delay τ to 10, and vector data V(i,m,j;k) are generated from pulse wave data measured in Step 31.

In Step 33, in the same manner as in Step 23 of FIG. 2, the maximum Lyapunov exponents λ1(i,m,j) and entropies E(i,m,j) are calculated, and are recorded in the recording unit 13 as the time series data on each i. When performing N sets of three-minute measurements, the time series data consisting of 3N data can be obtained.

In Step 34, Multiple Wavelet Resolution is performed as to the maximum Lyapunov exponents λ1(i,m,j) and the entropies E(i,m,j) derived in Step 33 to calculate time series waveforms of scaling coefficients S1(λ1) to S5(λ1) and S1(E) to S5(E), and of wavelet coefficients W1(λ1) to W5(λ1) and W1(E) to W5(E). Multiple Wavelet Resolution is a known analytical method for expanding a signal waveform in the orthogonal system, and the scaling coefficients and the wavelet coefficients are expansion coefficients.

Accordingly, the scaling coefficients S1(λ1) to S5(λ1) and the wavelet coefficients W1(λ1) to W5(λ1) as to the measurement data of the subject i are the first to fifth coefficients derived by Multiple Wavelet Resolution regarding the maximum Lyapunov exponents λ1(i,m,j) as time series data.

The scaling coefficients S1(E) to S5(E) and the wavelet coefficients W1(E) to W5(E) as to the measurement data of the subject i are the first to fifth coefficients derived by Multiple Wavelet Resolution regarding the entropies E(i,m, j) as time series data.

Figure 6:
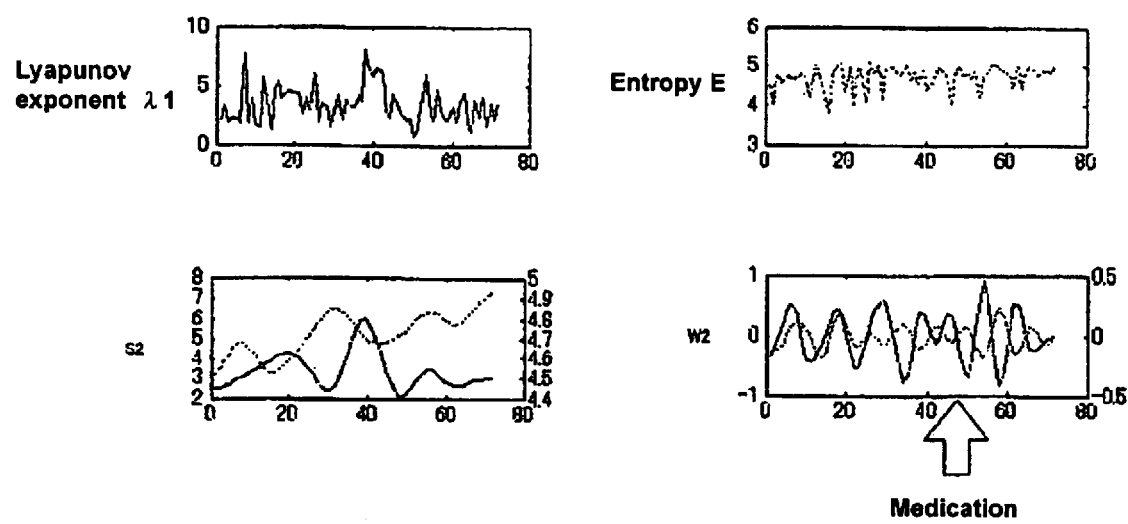
FIG. 6 shows a graph where a time series waveform of scaling coefficient $S2(\lambda 1)$ is overlaid upon a time series waveform of $S2(E)$ in the same measure, and graphs where a time series waveform of wavelet coefficient $W2(\lambda 1)$ is overlaid upon a time series waveform of $W2(E)$ in the same measure.

In Step 35, the scaling coefficients S1(λ1) to S5(λ1), S1(E) to S5(E) and the wavelet coefficients W1(λ1) to W5(λ1), W1(E) to W5(E) of the subject i are read out from the recording unit 13, regarded as time series data, and prepared on the video memory as image data of graphs shown in FIG. 6. In FIG. 6, each time series waveform of scaling coefficients S1(λ1) to S5(λ1) is overlaid upon a corresponding time series waveform of S1(E) to S5(E) at the same level, and each time series waveform of wavelet coefficient W1(λ1) to W5(λ1) is overlaid upon a corresponding time series waveform of W1(E) to W5(E) at the same level. The prepared graphs are displayed on the display unit 17.

In Step 36, the biological state of the subject i is evaluated based on the graphs resulting in Step 35. The evaluation is carried out according to the relation between each waveform of the scaling coefficients S1(λ1) to S5(λ1) and the corresponding waveform of S1(E) to S5(E) and the relation between each waveform of the wavelet coefficients W1(λ1) to W5(λ1) and the corresponding waveform of W1(E) to W5(E).

For example, the data measured before, during and after a medication are processed via the above-mentioned series of steps, consequently time series waveforms are displayed as to scaling coefficients S1 to S5, wavelet coefficients W1 to W5, Lyapunov exponent λ1 and entropy E, and then the effect of medication can be evaluated using the symmetry property between these waveforms as criteria. Specifically, if each waveform of the scaling coefficients S1(λ1) to S5(λ1) and the corresponding waveform of S1(E) to S5(E) vary symmetrically repeating intersections while each waveform of the wavelet coefficients W1(λ1) to W5(λ1) and the corresponding waveform of W1(E) to W5(E) vary symmetrically repeating intersections after medication, it can be judged that the medication is effective. In addition, it can be judged that the more symmetrical these waveforms to each other, the more effective the medication is.

FIG. 6 illustrates an example of the result obtained by processing as described above the waveforms of Lyapunov exponent and entropy before and after giving Agaricus to a cancer patient. Data measurements for 100 seconds were carried out from two to nine times per day over about three weeks. In FIG. 6, the upper two waveforms Orig. signal λ1 and Orig. signal E indicate the Lyapunov exponent λ1 and the entropy E of measurement data, respectively. The lower two waveforms indicate the scaling coefficient S2 and the wavelet coefficient W2, and the solid line indicates the coefficient of Lyapunov exponent λ1, and the dashed line the coefficient of entropy E.

These figures show that the waveforms are less symmetric before the administration indicated by the arrow and more symmetric after the administration. It has been shown that the administration of Agaricus has an effect of enhancing the symmetric dynamism of the two indices during a certain period of time. This effect was well in agreement also with the clinical symptom.

Embodiment 3

Correlation Analysis Using DFA Method

The judging method using an analytical method of correlation, i.e. DFA method, is described below. DFA (Detrended Fluctuation Analysis) method was introduced by Buldyrev in 1993 as an index for judging how two fluctuation signals that are apparently random are analogous. The method is to plot the standard deviation of two signal waves that fluctuate in a random manner, while changing the ranges to be compared flexibly. The signal waveform derived from magnification of one fluctuation signal is compared with the original signal waveform by the DFA method, by which the self-similarity, i.e., fractal nature of this fluctuation signal can be evaluated. However, since the signal from an actual living body has an unsteady fluctuation, it was difficult to carry out an indexation of this fractal nature.

This became possible due to the idea of Goldberger et al. in 1995 of setting the targets to be compared as the local average value. This is expressed as following two equations.

$$y(k) = \sum_{i=1}^{k} [B(i) - B_{ave}] \quad \text{[Formula 6]}$$

Here, y(k) is the whole trend, B(i) the i-th value, and $B_{ave}$ the average value.

Each divisional trend is subtracted from the whole trend, and F is calculated by the following formula. The resulting F is considered proportional to the power of the divided region, which is called as Power-law.

$$F(n) = \sqrt{\frac{1}{N} \sum_{k=1}^{N} [y(k) - y_n(k)]^2} \propto n^\alpha \quad \text{[Formula 7]}$$

Here, $y_n(k)$ is a trend of the divided part.

Using this F(n), a self-similarity dimension α is calculated from the slopes of graphs of log F(n) and log n.

In this embodiment, Lyapunov exponent and entropy are computed, for example from the time series data of the biological signal based on a pulse wave, and the self-similarities of the Lyapunov exponent and the entropy are calculated by DFA method. This correlation is determined by the self-similarity dimension α.

The self-similarity dimension α has a certain relation to an auto correlation coefficient and indicates the followings:
when $0 < \alpha < 0.5$, the anti-correlation where α is not derivable from the graph;
when $\alpha = 0.5$, uncorrelated (white noise);
when $0.5 < \alpha < 1.0$, the persistent long range correlation;
when $\alpha = 1.0$, the 1/f fluctuation or the noise;
when $\alpha > 1.0$, the state where Power-law indicating fractal nature or self-similarity is lost; and
when $\alpha = 1.5$, Brown noise.

Therefore, it is shown that the self-similarity dimension α of Lyapunov exponent is useful for the judgement of a biological state. The self-similarity dimension α of Lyapunov exponent takes a value 1.0 in a normal state, and the closer α approaches to 1.0, the better the state is. The self-similarity dimension α of entropy takes a value 1.5 in a normal state, and the closer α is to 1.5, the better the state is.

There is a case example of a certain slight depressive patient where α varied from 0.563 (before treatment) to 0.767 (after treatment). Thus it is shown that in addition to the evaluation of the α value itself, the directional property of a variation, that is, the direction of α value variation before and after an action on a living body, is also useful for the judgement.

Figure 7:
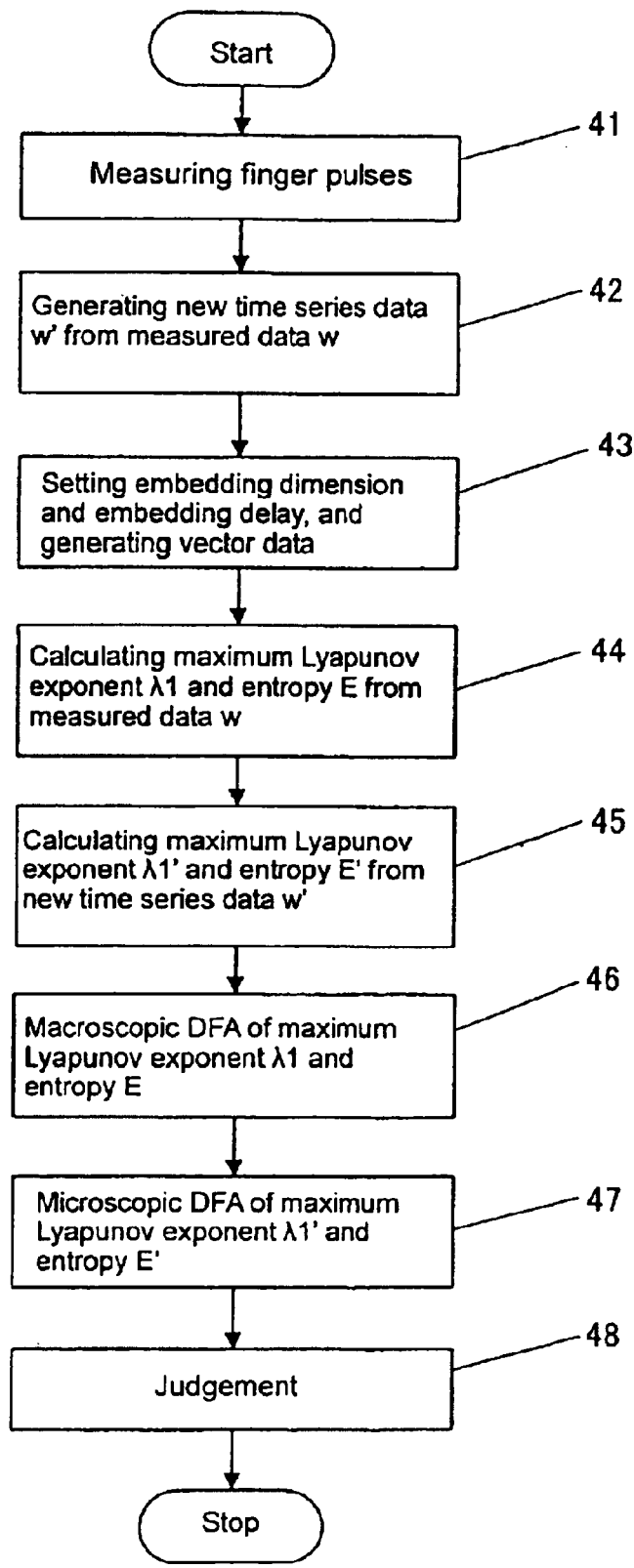
FIG. 7 is a flow chart showing the processing executed by CPU 11 in the judging method for a biological state using Power-law, i.e., DFA method, performed in the apparatus for judging a biological state shown in FIG. 1.

FIG. 7 is a flow chart showing the processing executed by CPU 11 in the judging method for a biological state using Power-law, i.e. DFA method, performed in the judging apparatus for a biological state shown in FIG. 1.

In the same manner as in Step 21 of FIG. 2, finger pulse data are measured and recorded on the recording unit 13 in Step 41. Only measurements of a specific subject i are performed in this embodiment, where three times of a three-minute measurement are regarded as one set, three sets are as one round. Three or more rounds, i.e., 27 or more times in total of measurements are performed. In the following, m1(m1≧3) represents a set number, m2(m2≧3) a round number, and the measurement data is expressed as w(i,m2,m1,j;k). In each processing, calculation is carried out in the memory unit 12 and the calculation result is recorded in the predetermined area of the recording unit 13.

In Step 42, as to the measurement data read out from the recording unit 13, successive 5000 data w(i,m2,m1,j;k1) to w(i,m2,m1,j;k1+5000), which are from the time series data {w(i,m2,m1,j)} consisting of 36000 pieces of data resulting from one measurement, are recorded in the recording unit as a new time series data {w'$_n$(i,m2,m1,j)}. Here, each first data of the 5000 successive data is obtained by shifting the first data of the original 36000 time series data {w(i,m2,m1,j)} by one second (200 data) repeatedly. Consequently, 156 pieces (=1+(36000−5000)/200) of new time series data {w'$_n$(i,m2,m1,j)} (n=1 to 156) are prepared from one time series data {w(i,m2,m1,j)} by shifting the first data by one second sequentially. The shift of the start position of data is called as Bernoulli's shift.

In Step 43, in the same manner as in Step 23 of FIG. 2, an embedding dimension is set to four and an embedding delay τ to 10, generating vector data V'(i,m2,m1,j,n;k) (k=1 to 5000) with respect to the new time series data {w'(i,m2, m1,j,n)} (n=1 to 156).

In Step 44, the maximum Lyapunov exponents λ1(i,m2, m1,j) are calculated from the Formula 2 and entropies E(i,m2,m1,j) from the Formula 3 with respect to the measurement data w(i,m2,m1,j;k), in the same way as in Step 23 of FIG. 2.

In Step 45, the maximum Lyapunov exponent λ1'(i,m2, m1,j,n)), i.e. the highest value among 4 Lyapunov exponents λ(i,m2,m1,j,n) derived from the Formula 2, and the entropy E(i,m2,m1,j) from the Formula 3 are calculated with respect to each {V'(i,m2,m1,j,n)} (n=1 to 156), in the same manner as in Step 44.

For example in the case of carrying out three times of three-minute measurement for three rounds, 27 pieces (=m2×m1×j×n, m1=m2=j=3) of time series data of maximum Lyapunov exponents {λ1'(i,m2,m1,j)} and 27 pieces of time series data of entropies E'(i,m2,m1,j,n) are obtained.

In Step 46, macroscopic DFA method is carried out as to 27 maximum Lyapunov exponents λ1(i,m2,m1,j) and 27 entropies E(i,m2,m1,j) which were calculated in Step 44, and then the fractal self-similarity structure is analyzed. Accordingly, time series data B(i) are taken for λ1(i,m2,m1, j) in the above-mentioned Formula 6, and α to satisfy the Formula 7 is calculated as $α_{λ1}$. Similarly, time series data B(i) are taken for E(i,m2,m1,j) and α to satisfy the Formula 7 is calculated as $α_E$.

In Step 47, microscopic DFA method is carried out with respect to 27 time series data {λ1'(i,m2,m1,j)} and 27 time series data {E'(i,m2,m1,j)}, which were calculated in Step 45 and each consisting of 156 pieces of data, and the fractal self-similarity structure is analyzed.

Accordingly, time series data B(i) are taken for λ1'(i,m2, m1,j,n) in the above-mentioned Formula 6 to calculate $α_{λ1}$'(i,m2,m1,j) that satisfies the Formula 7. Similarly, time series data B(i) are taken for E'(i,m2,m1,j,n) to calculate $α_E$'(i,m2,m1,j) that satisfies the Formula 7. N=156 here. Thus 27 pieces each of $α_{λ1}$'(i,m2,m1,j) and $α_E$'(i,m2,m1,j) are derived.

In Step 48, the effect of medication is judged by the variability with time of α calculated in Steps 46 and 47.

For example, as to the data measured over the determined period before and after the medication, $α_{λ1}$' and $α_E$' calculated in Step 46 are plotted with time base on the horizontal axis to prepare a line graph. The variation of the line graph before and after the medication is evaluated microscopically and then the effectiveness of medication can be judged.

In addition, as to the data measured over the determined period before and after the medication, $α_{λ1}$ and $α_E$ calculated in Step 46 are compared between before and after medication and then the effectiveness of medication can be judged.

Figure 8:
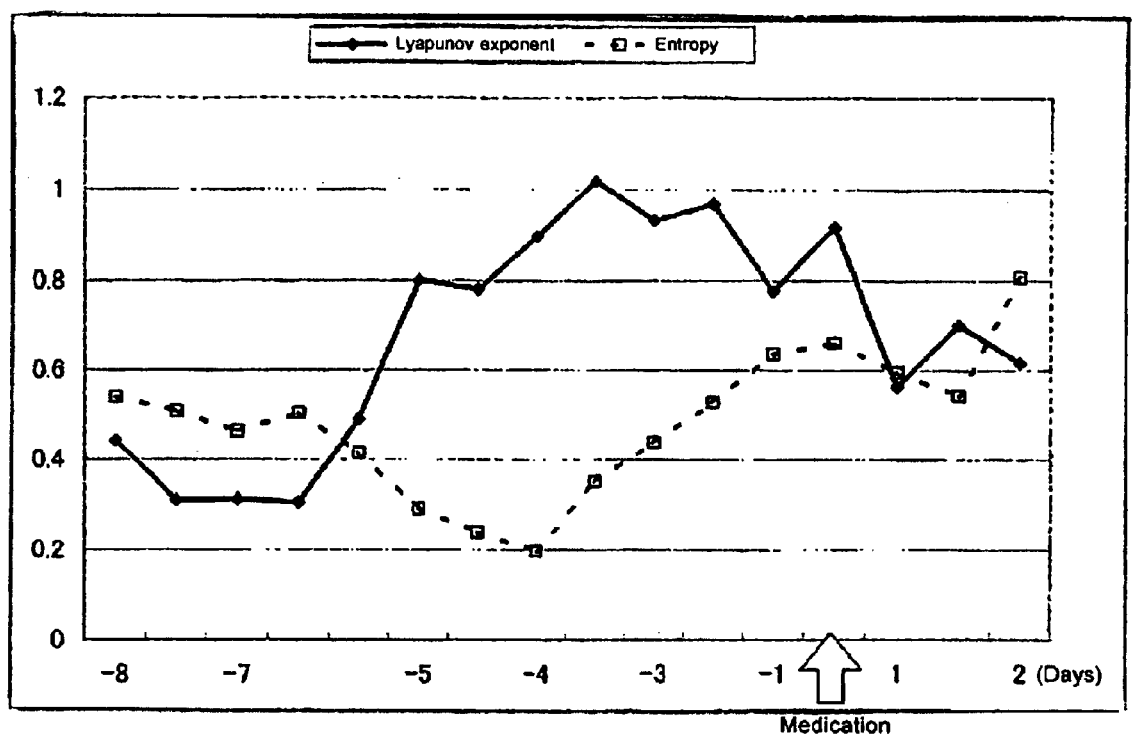
FIG. 8 shows a result of macroscopic DFA method of the same medication experiment data shown in FIG. 6.

In the above-mentioned second embodiment, it was illustrated that the medication effect at the time of administering Agaricus to a cancer patient can be judged (see FIG. 6). FIG. 8 shows the result of macroscopic DFA method of the same medication experiment data. The 27 pieces of self-similarity dimensions α derived from the time series data of Lyapunov exponent and entropy are expressed by a point and plotted while being shifted every three pieces, with the vertical axis α in FIG. 8. Thereby, tracing of the medication effect on an hour-by-hour basis became possible.

As shown in FIG. 8, the variation in the symmetry of Lyapunov exponent and entropy, which was observed in FIG. 6, changes dynamically by the administration of Agaricus, and the highest entropy value is recorded. However, since the state where a Lyapunov exponent is somewhat low continues, the limit of the effect of Agaricus is also shown.

As described above, it is possible to judge a biological state and a medication effect on a subject i by using the finger pulse data measured from the subject i to calculate $α_{λ1}$(i), $α_E$(i), $α_{λ1}$'(i), and $α_E$'(i) as to maximum Lyapunov exponents λ1 and Entropies E and observing the variation with time of these values. For example, when $α_{λ1}$(i) and $α_{λ1,n}$(i) approach 1, the state of a living body can be judged as being near the 1/f noise state, i.e. being good. When $α_E$(i) and $α_{E,n}$(i) approach 1.5, the state of a living body can be judged as being near the Brown noise state, therefore the medication can be judged as effective. As stated above, an effective judgement is possible if a finger pulse is measured 27 times or more per one subject, more preferably 54 times or more.

Embodiment 4

Method Based on Ratio of Higuchi Fractal Dimensions (D1/D2): F-symmetry Method

A judging method using F-symmetry method is described below.

A living body is known to exhibit unsteady chaotic nature and multi-fractal structure. Two indices D1 and D2 called Higuchi fractal dimension can express the multi-fractal nature of a system, which will be described later in detail. The present inventors carried out an analysis of about 40 healthy people and found that the ratio of these two indices (D1/D2) correspond with the Feigenbaum constant that is called universal constant.

Figure 9:
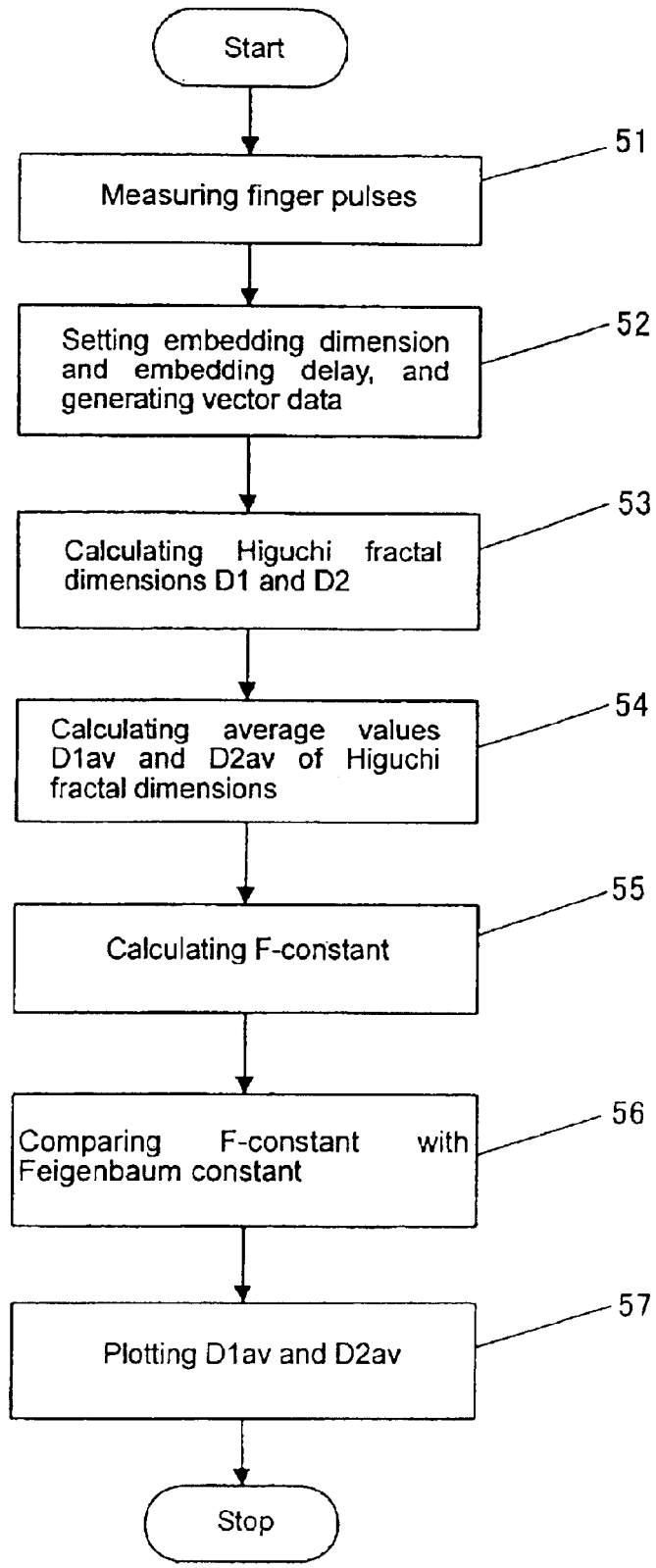
FIG. 9 is a flow chart showing the processing executed by CPU 11 in the judging method for a biological state using Higuchi fractal dimension performed in the apparatus for judging a biological state shown in FIG. 1.

FIG. 9 is a flow chart showing the processing executed by CPU 11 in the judging method for a biological state using Higuchi fractal dimension performed in the apparatus for judging a biological state shown in FIG. 1.

In Step 51, in the same manner as in Step 21 of FIG. 2, finger pulse data are measured and recorded in the recording unit 13. Only measurements of a specific subject i are performed in this embodiment.

In Step 52, in the same manner as in Step 22 of FIG. 2, an embedding dimension is set to 4, an embedding delay τ to 10, and a vector data V(i,j,k) are generated from pulse wave data measured in Step 51.

In Step 53, Higuchi fractal dimension D is calculated as to the measurement data of each time. Higuchi fractal dimension D is defined by Formula 8, and represents the complexity of the shape of time series data regarded as a one-dimensional geometric structure.

$$D(t) = -\frac{\log\Delta_t - \log\Delta_{t-1}}{\log t - \log(t-1)} \quad \text{[Formula 8]}$$

wherein $$\Delta_t = \frac{1}{N-1}\sum_{k=1}^{N-t} \Delta_t^k$$

$$\Delta_t^k = \frac{Lt}{N-1}\sum_{i=1}^{\left[\frac{N-k}{t}\right]} |S_{k+it} - S_{k+(i-1)t}|$$

$$Lt = \left[\frac{N-k}{t}\right]t$$

$t = 1$ to $N/2$ (integer), and [ ] (square bracket) expresses the maximum integer which does not exceed the value in the square bracket, S is finger pulse data of each measurement, and N is the number of data (=36000).

Figure 10:
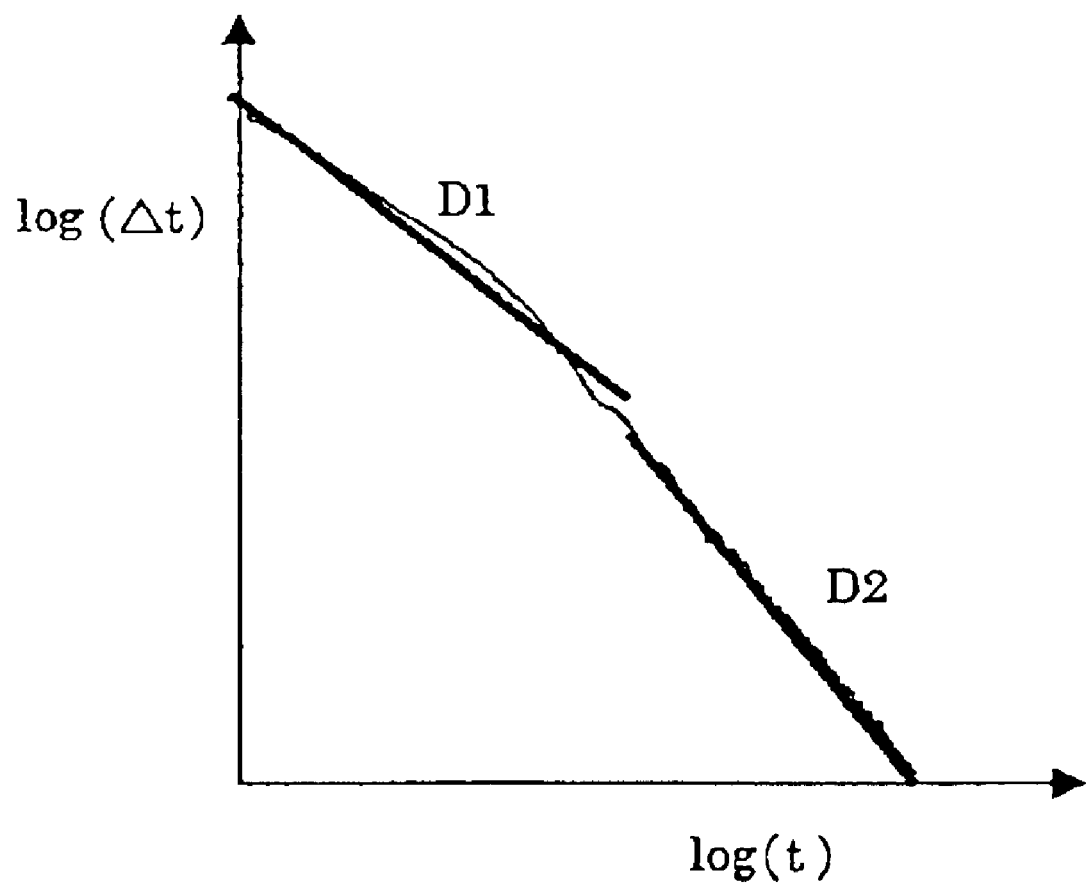
FIG. 10 indicates D1 and D2 of Higuchi fractal dimension D.

As shown in Formula 8, Higuchi fractal dimension D is a function of t. As shown in FIG. 10, a graph with log (t) on the horizontal axis and log ($\Delta_t$) on the vertical axis as to finger pulse data roughly is approximated by two straight lines each having a fixed slope. Formula 8 shows that Higuchi fractal dimension D corresponds with the slope. Accordingly, let the slope in each area be Higuchi fractal dimension D1(i,j) or D2(i,j) of each area. The slope of a graph is calculable by the well-known method, for example, least-squares method.

In Step 54, the average values of three-time measurements of the subject i, D1av(i) and D2av(i), are calculated as to D1(i,j) and D2(i,j) derived by the processing in Step 53.

In Step 55, F-constant F(i) is calculated by Formula 9.

$F(i)=(D2av(i)+D1av(i))/(D2av(i)-D1av(i))$ [Formula 9]

In Step 56, F-constant F(i) and Feigenbaum constant (F=4.6692) which were calculated in Step 55 are compared, and it is judged whether the difference between the F-constant F(i) and the Feigenbaum constant is below a specified value. Feigenbaum constant, which was studied by M. J. Feigenbaum, is a universal constant drawn by the following ratios $\delta$ of two branch structures that are the mechanisms of chaos generation.

$$\delta = \lim_{n\to\infty} \frac{R_n - R_{n-1}}{R_{n+1} - R_n} = 4.669201609 \ldots$$

The details are explained, for example, in "Chaos Primer—analysis and mathematical principle of phenomenon" written by Hiroyuki Nagashima and Yoshikazu Baba, published by Baifukan.

In Step 57, a graph, on which two or more straight lines having a constant F(i) are drawn with D1av(i) on the horizontal axis and D2av(i) on the vertical axis and D1av(i) and D2av(i) calculated in Step 54 are plotted, is prepared in the video unit 15.

Figure 11:
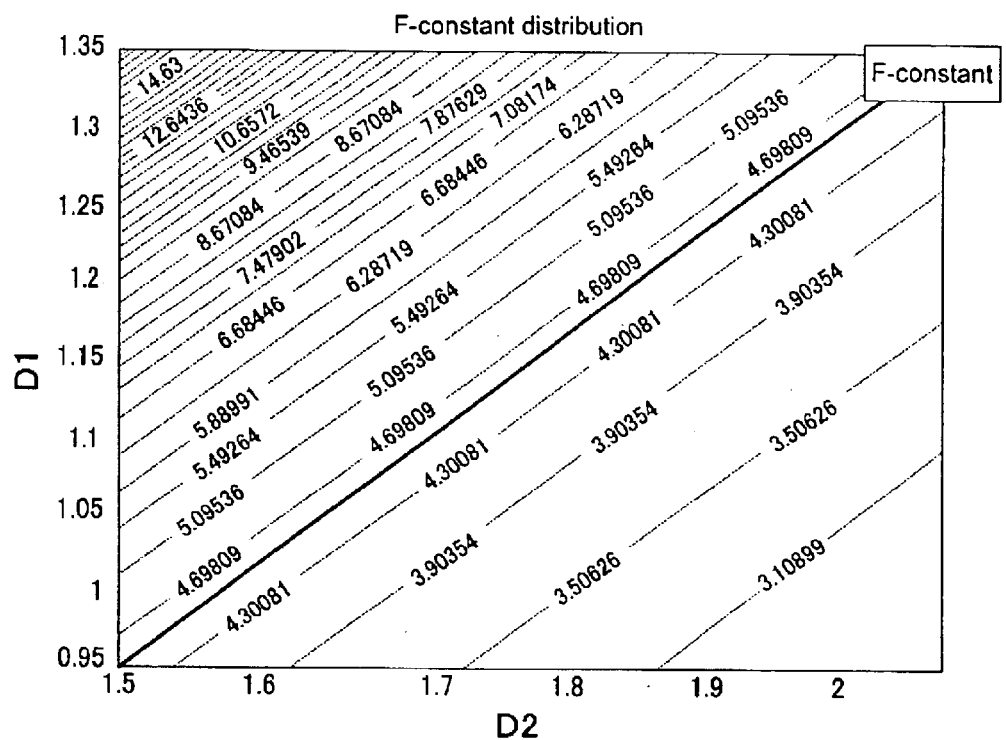
FIG. 11 is a graph showing straight lines corresponding to each of constant F value.

Formula 9 is transformed as follows:

$D2av(i)=D1av(i) \cdot (F(i)+1)/(F(i)-1)$ which indicates the straight line having a slope of (F(i)+1)/(F(i)-1) when F(i) is assumed to be a constant value. The two or more straight lines drawn above have this slope and contain a straight line corresponding to Feigenbaum constant. FIG. 11 is a graph showing straight lines each corresponding to a constant F value.

As described above, in Step 56, the judgement of the biological state of the subject i can be carried out by comparing F-constant F(i) with Feigenbaum constant.

The judgement of the biological state of the subject i can be also carried out by evaluating the physical relationship between the points plotted in Step 57 and the Feigenbaum constant line.

Figure 12:
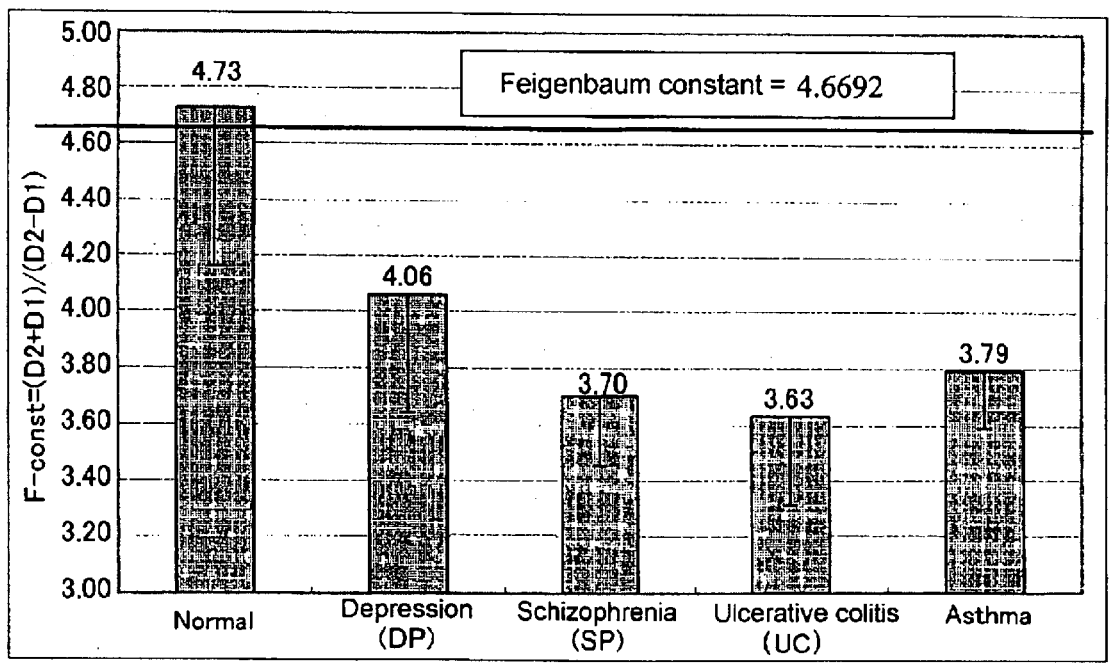
FIG. 12 shows a result of the comparison in Step 56.
Figure 13:
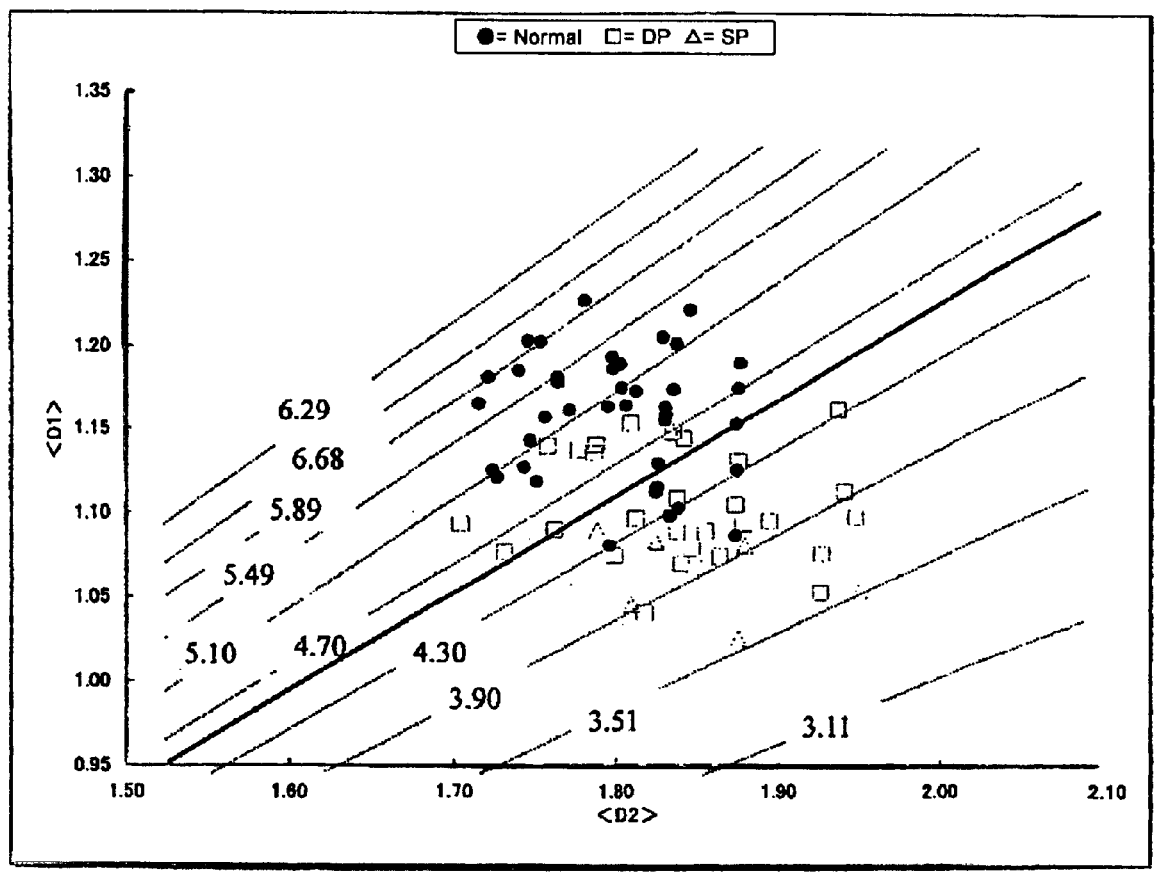
FIG. 13 is a graph made in Step 57.

FIGS. 12 and 13 are graphs showing one example result of repeating Steps 51–57 on two or more subjects. FIG. 12 shows a comparison result of Step 56, and FIG. 13 shows a graph prepared in Step 57.

In FIG. 12, the average values of the data from a normal person and a patient of depression, schizophrenia, asthma or chronic ulcerative colitis are indicated by bar graphs. F-constant is 4.73 for a healthy person (Normal), 4.06 for depression (DP), 3.70 for schizophrenia (SP), 3.63 for chronic ulcerative colitis (UC) and 3.76 for asthma (Asthma). It is clear from FIG. 12 that a healthy person has a F-constant close to the Feigenbaum constant line and sick subjects have the ones far away from the Feigenbaum constant line. It also turns out that F-constant shows a specific value according to the kind of disease.

FIG. 13 is a graph where the data from normal persons, patients of depression and schizophrenia are plotted. It is shown that the data from normal persons are distributed near the Feigenbaum constant line and especially the data from schizophrenia patients are distributed away from the Feigenbaum constant line.

A F-constant corresponding to each of these diseases can be derived by the calculation of F-constant as to the group of patients having the same disease. The larger the number of patients to be measured (population), the more the calculation of F-constant value as to each disease accurate. Accordingly, a more accurate judgement is attained by storing data through an Artificial Neural Network.

Moreover, determining the symmetric property in the distributions of Higuchi fractal dimensions D1 and D2 obtained by F-symmetry method and combining it with said correlation and symmetry analyses, a biological state can be judged with higher accuracy. For example, as described in the first embodiment, the symmetry analysis of Lyapunov exponent and entropy using F-symmetry method resulted in 83% of distinguishability with respect to the group shown in FIG. 4. However, in addition of F-symmetry method to the evaluation using the same measurement data, 97% of distinguishability was achieved.

Although the subjects having comparable F-constants (for example, F-constants of SP and GLY are the same at 3.70) cannot be classified by means of only F-symmetry method, it becomes possible by additionally using the Mirror value and the correlation dimension determined by DFA method.

Embodiment 5

Judging Method for Efficacy of an Action That May Affect a Biological State of a Living Body Taking for an example the case where the action that may change a biological state is a medication, described below is a judging method for the symmetric property of Lyapunov exponent and entropy directly from the graph where the variations of these exponents with time are recorded.

In the judging method according to this embodiment, when the action that may change a biological state is a drug medication, the effectiveness of the drug can be judged. If a judgement is carried out as to two or more drugs with the judging method according to this embodiment, in the early stages of drug medication it can be judged which drug is more effective. The effect of combined use (synergy) effect of drugs can also be judged by using two or more drugs together.

As shown in FIG. 14, symmetrical variation of entropy and Lyapunov exponent (if one decreases, another will increase) generally indicates a normal living state. This means, in other words, there exist fluctuations in the difference between Lyapunov exponent and entropy, and such a state can be called "mirror dynamic". As shown as an illustrative example in FIG. 15, the fluctuation in the difference (shadow area) of Lyapunov exponent and entropy is great in the early stages of treatment for Patient A, indicating that the effectiveness of combined medication of amoxapine (23 mg×3) and imipramine (10 mg×6) to Patient A is high. On the other hand, the fluctuation in the difference (shadow area) of Lyapunov exponent and entropy is minor in the early stages of treatment for Patient B, and therefore it can be judged that the effectiveness of medication of cloxazolam (1 mg) is low.

On the other hand, another criterion of the judging method according to this embodiment is the directional property of temporal variation of the difference between entropy and Lyapunov exponent. When the variation of the difference shows the direction that alternately increases and decreases, the effectiveness of the drug is high. When such "fluctuation" is not observed in the variation in the difference, the effectiveness of the drug is judged to be low.

In the method according to this embodiment for judging the efficacy of an action, measurements of Lyapunov exponent and entropy are carried out at least twice, i.e. before and after the medication. As to the measurement after drug medication, it is preferred to measure at least twice, although one measurement is sufficient. Among the measurements carried out at least twice, at least one measurement may be after the medication, during or after the period when the drug is expected to take effect. The period when the drug is expected to take effect is, for example, the period when the blood level of drug is expected to reach an effective level after medication. The period after the drug is expected to take effect is, for example, the period when the blood level of drug is expected to decrease below an effective level. The measurements carried out at least twice may be carried out as follows: at least twice during the period when the drug is expected to take effect; at least once during the period when the drug is expected to take effect and at least once after said period; or at least once during the period when the drug is expected to take effect and at least once before or after medication when the blood level of drug does not reach an effective level yet. Lyapunov exponent and entropy measured at least once after the medication are compared to the results before the medication, the variation in the symmetric property between the Lyapunov exponent and the entropy and the directional property of temporal variation in the difference between the Lyapunov exponent and the entropy, and then the effectiveness of the drug can be judged. When it takes time before the values of Lyapunov exponent and entropy vary under the influence of drug medication, the values at several dozen minutes to hours or in some cases a little over ten hours to several days immediately after drug medication are used as initial values, and the initial values may be compared to Lyapunov exponents and entropy values of a certain period of time after the medication.

Measurements of Lyapunov exponent and entropy may be carried out twice. For example, when taking a drug every day, the measurements may be carried out for several successive days or several times after a certain period of time.

Embodiment 6
Judging System for a Biological State

In the above, the cases where a biological state or a pharmaceutical effect is judged by the main unit 10 of judging apparatus are explained. Explained here is a case where data measurement and judging process are respectively performed in different pieces of apparatus. The judging system of a biological state according to this embodiment comprises the main unit 10 provided with a communication interface (not shown in FIG. 1) and an analysis computer for performing a judgement process installed in a place distant from the main unit 10. The main unit 10 is connected to a telephone line, a network line or like communication lines by the communication interface, and the data measured in the detection unit 20 and saved in a specified file format at the recording unit 13 is transmitted via a communication line to the analysis computer connected to the communication line. According to the above-mentioned method, the analysis computer carries out calculation processing of the received measurement data, and the judgement of a biological state etc. is carried out.

In order to reduce the amount of data to be communicated, it is possible to carry out data measurement and a part of judgement processing by the main unit 10 in a judging apparatus and the remaining judgement processing by the analysis computer. For example, in the first embodiment, it is possible to carry out the processing of Steps 21–26 by the main unit 10 of a judging apparatus, and the resulting weighted Lyapunov exponents $\lambda 1w$ and Entropies E are transmitted, and the processing of Steps 27–28 can be carried out by the analysis computer. For example, when carrying out three-minute measurement of each subject for three times with a sampling period of 5 milliseconds (msec) and treating one measurement data by 1 byte, the main unit 10 of judging apparatus processes 36000×3 bytes, i.e. about 108 kilobytes of data per each subject. On the other hand, the number of the resulting weighted Lyapunov exponents $\lambda 1w$ and Entropies E is three respectively, and the data to be communicated is only 6 bytes per each subject. For this reason, it is very efficient and the data of a large quantity of subjects can be exchanged more easily.

The result of judgement carried out by the analysis computer as to the data transmitted from each main unit 10 in a plurality of client sites can be associated with the number given uniquely to each main body 10, which can be saved and controlled as a database. It is also possible to transmit the judgement result, which is converted into a specified data format, to the main unit 10 of a corresponding client via a communication line or the like. Transfer of data can be carried out also by conveying the recording medium recording the data, without using a communication line.

The cases where the 1st to the 5th embodiments are independently performed are focused above, however, it is also possible to combine these judging method. As explained in the 4th embodiment, by such combination, judgements on a biological state and on the efficacy of the action that may affect a biological state can be more reliable.

In the above 1st to 4th embodiment, a data sampling period, time of one measurement, the number of measurements per one set, and the number of sets per one round are not limited to the above-mentioned values and can be changed according to the performance of a measuring apparatus etc, or as far as one measurement takes neither too much time nor too much computation time. An embedding dimension and an embedding delay are also not limited to the above-mentioned values and can be changed as far as computation time does not become too long.

In the 1st embodiment, the offset values to separate the eight regions into two groups are not limited to the above-mentioned values, but can be other two different values. In addition, the eight regions are separated into not only two groups, but also can be separated into more groups and offset values corresponding to each can be set.

In the 2nd embodiment, each five pieces of coefficients selected from the lowest order are used as scaling coefficients and wavelet coefficients. However, it is also possible to use the coefficients of higher orders, and it is also possible to use less than five coefficients although the accuracy of judgement becomes low.

In the 3rd embodiment, explained was the case where 5000 pieces of data are extracted from actual measurement data to be used as new time series data. However, as long as successive data is extracted from actual measurement data, the number of data may not be limited to 5000 pieces but can be other number. The interval to shift the first data to be extracted, i.e., the time interval of Bernoulli shift, is not limited to one second.

In each embodiment, the last step to judge a state of a living body can also be carried out by an Artificial Neural Network. For example, a hierarchical type Artificial Neural Network provided with an input layer, an interlayer and an output layer can be used, in which the coupling coefficients (coefficients for determining an output value from the input value to each neuron) of the interlayer neuron is corrected according to learning based on the error back propagation. For example, an input layer can comprise four neurons into which the average value of the weighted maximum Lyapunov exponents $\lambda1wav(i)$ of the 1st embodiment, the self-similarity dimensions $\alpha_{\lambda 1}$ and $\alpha_E$ of the 3rd embodiment, and the F-constant $F(i)$ of the 4th embodiment are each inputted, and an output layer can comprise two neurons each corresponding to a normal state or disease. Thus constituted Artificial Neural Network is made to learn the measurement data as teacher data, from the population whose judgement results are definite, and then a highly precise synthetic judgement can be carried out automatically.

As described above, according to the 1st to the 5th embodiments, it is possible to judge the state of a living body. In particular, according to the 1st to the 4th embodiments 1 to 4, it is more effective in that the biological state at the time of measurement can be judged by one measurement.

According to the 1st to the 5th embodiments, the action intended to improve a biological state or the action that may cause a bad influence on a biological state is carried out after this first judgement. In case of judging the degree of improving effect on the biological state by the action, the biological state is judged after carrying out the action and the biological states before and after the action are compared to judge the efficacy of the action. In said judgement of the efficacy of the action, the biological state after the action can be judged simultaneously.

As examples of a biological state that can be measured, a mental state or a physical state of normality, morbidity, and non-morbidity (not a normal state and prior to morbidity) of a subject are illustrated. Examples of the mental state may include morbidity like mental and/or nervous diseases such as depression, mania, manic-depressive illness, psychosomatic disease, schizophrenia, neurotic, insomnia, epilepsy, Parkinson's disease, hallucinosis, autism, and non-morbidity symptoms, such as uneasiness, impatience, oversensitivity, excitement, neuralgia, despondency, giddiness, headache, mental fatigue, withdrawal and the like. Examples of the physical state may comprise cancer, cardiovascular-system diseases such as angina, myocardial infarction, cerebral infarction, high blood pressure, hyperlipemia, abnormal heart rhythm, hypercholesterolemia and the like, chronic hepatitis, liver cirrhosis, gastric ulcer, pancreatitis, diabetes, chronic nephritis, allergic diseases, infection diseases of viruses, bacterium, fungi and the like, ophthalmologic diseases such as cataract, glaucoma and the like, infertility, fracture, lumbago, stiffness of the shoulders, external wound, etc., or the physically ill-being state in the stage prior to such physical diseases.

When diagnosed as having such a disease or mentally or physically ill condition, preventive or therapeutic action on diseases such as drug medication, dialysis, use of medical implements (e.g., radiation or laser irradiation, treatment by electric/magnetic pulse, rehabilitation, etc.), an uptake of food that may ameliorate the state of a living body, and the action of adding a physical or mental stimulus can be carried out.

The judgement of the efficacy of this action on the biological state can be carried out about 1 hour to 10 days after taking such an action. The judgement of a biological state after taking the action may be conducted just once or more times. When the action is judged to turn a biological state into a normal state (positive), said action will be carried out continuously. Other actions will be chosen when the biological state is judged unchanging (neutral) or getting worse (negative).

The drug to be judged for its efficacy comprises drugs to treat all kinds of diseases, for example, therapeutic agents for diseases associated with immunity/hormone/ and neural system. Specific examples are antibacterial agents, antivirotics, antifungals and like drugs against pathogenic organisms, antitumor agents, immunosuppressants, antiinflammatory agents, anti-allergy agents, therapeutic agents for diabetes, hormone drugs, vitamin preparations, infusions, blood products, anti-thrombotic agents, antihyperlipidemic drugs, hemostatics, hematinics, cardiotonics, anti-arrhythmic drugs, therapeutic agents for angina, a vasodilators, depressors, diuretics, bronchodilators, therapeutic agents for digestive ulcer, intestinal remedy, therapeutic agents for liver diseases, therapeutic agents for pancreatopathy, sleeping pills, analgesic agents, antiepilepsy drugs, psychotropic drugs, antianxiety drugs, autonomic agents, Parkinson's disease drugs, local anesthetics, agents for ophthalmology, agents for dermatology, etc.

The food that may ameliorate the state of a living body may comprise a so-called supplement, and the food is supplied in the form of solid or beverage. Examples of the food are an extract or a foodstuff containing vitamins or substances known to have a reducing action on blood pressure, blood cholesterol, fat, blood sugar, etc., a nourishing and sustaining action, a preventing action on aging, a reducing action on body-weight or the like.

Examples of the physical stimulus comprise physical exercise, massage, acupuncture and moxibustion, changes of temperature (high temperature or low temperature) and the like, and examples of the mental stimulus comprise music, conversation including counseling, reading and the like.

Figure 16:
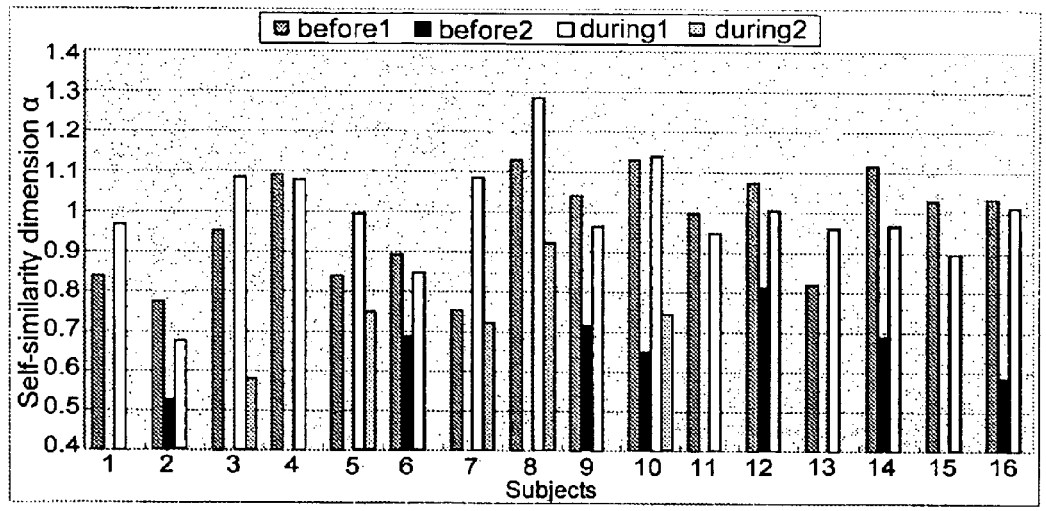
FIG. 16 is a graph showing the self-similarity dimension $\alpha$ derived by applying DFA method to time series data of pulse waves obtained from 16 subjects of different age and sex listening to their most favorite music.

For example, the efficacy of musical therapy, the active state of the human right and left brain, etc. can be judged. FIG. 16 is a graph showing the self-similarity dimension $\alpha$ derived by applying DFA method to time series data of pulse waves obtained from 16 subjects of different age and sex listening to their most favorite music. These 16 persons include a healthy person, those who have a disease, those who had a disease, a person with sufficient physical condition, and a person with bad physical condition. As a result of analysis, especially in the person with bad physical condition, a great variation is observed in a fluctuation index, and $\alpha$ approaches 1.0 by listening to music, that is, the fluctuation of autonomic nerves approaches the 1/f law.

Figure 17:
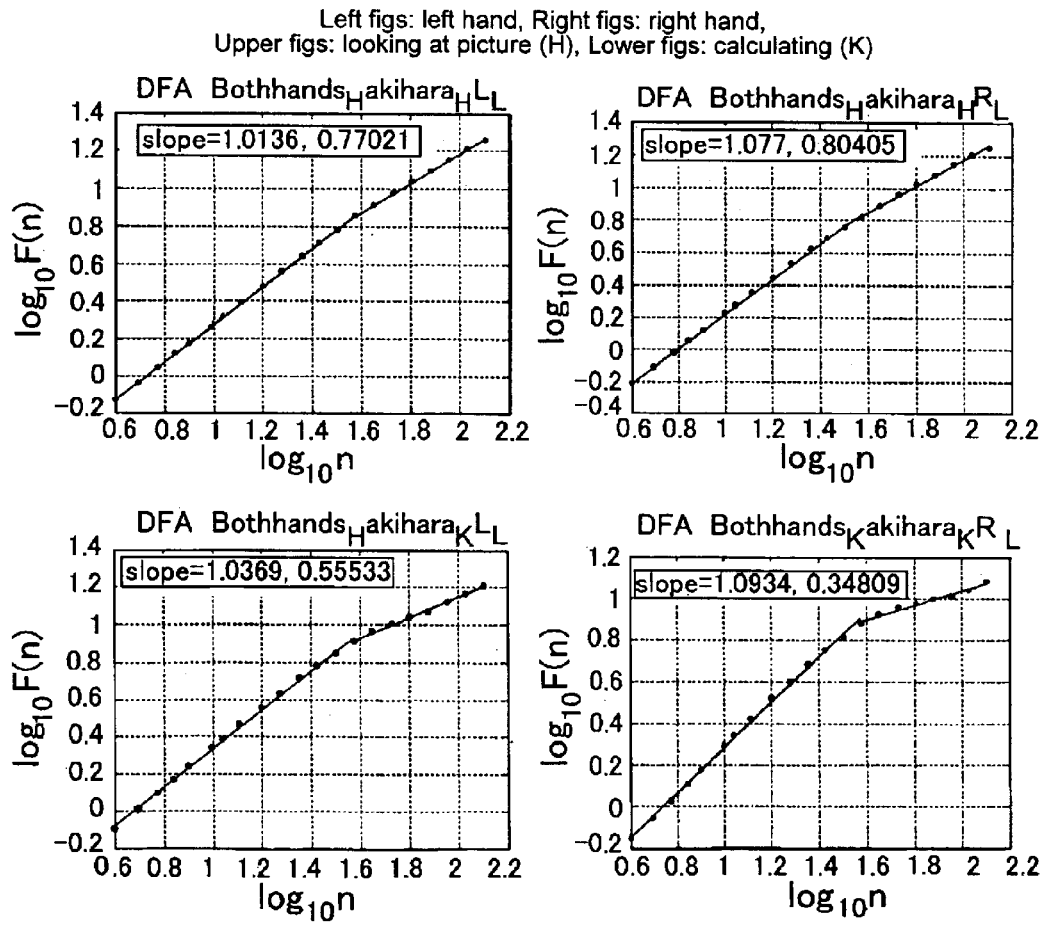
FIGS. 17 and 18 show the results of DFA method of finger pulses from the right and left hands of a subject while looking at a picture or calculating.
Figure 18:
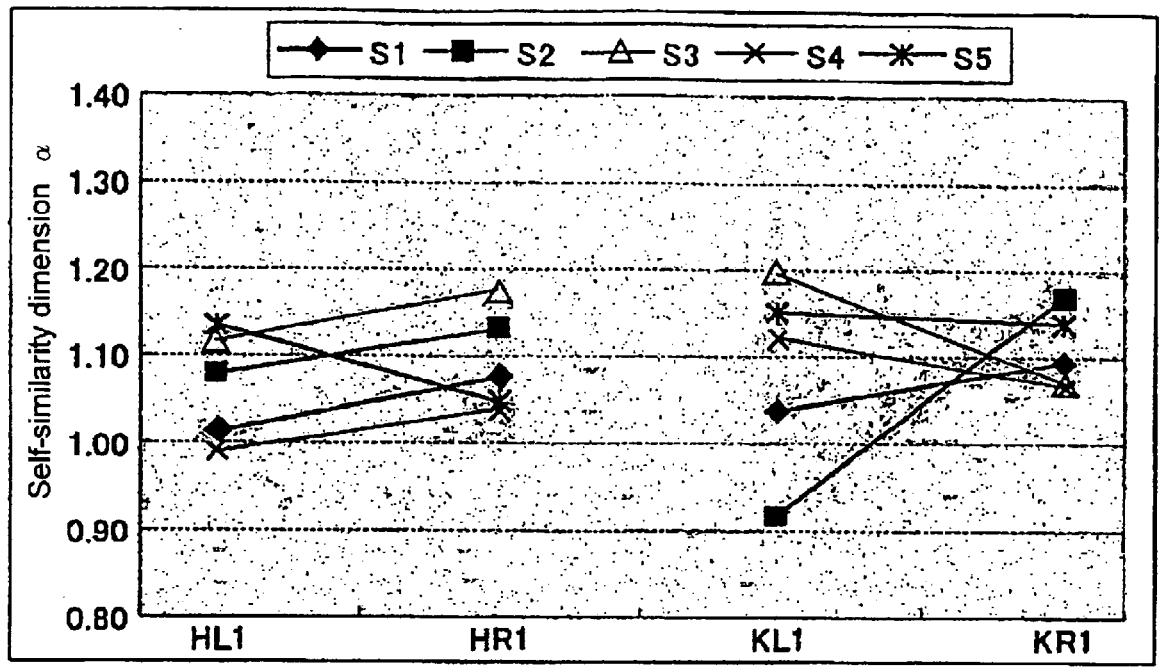

FIGS. 17 and 18 show the results of DFA method of finger pulses from the right and left hands of a subject while looking at a picture or calculating. The notation of FIG. 17 is the same as that of FIG. 19, and the slope of graph indicates the self-similarity dimension $\alpha$. The two upper and lower graphs in the left or right side resulted from analyzing the finger pulse data of left or right hand, respectively. The two upper and lower graphs are obtained by analyzing the finger pulse data in a period of looking at a picture or carrying out calculation, respectively. FIG. 18 shows a graph of the self-similarity dimension α as a result of analyzing the finger pulse data obtained from five subjects under the similar experiment. As shown in FIGS. 17 and 18, the active state of left and right brain can be observed as a variation of the self-similarity dimension α.

The embodiments according to the present inventions were described in the above. In the following, actual application examples of the present invention will be explained.

EXAMPLE 1

Figure 19:
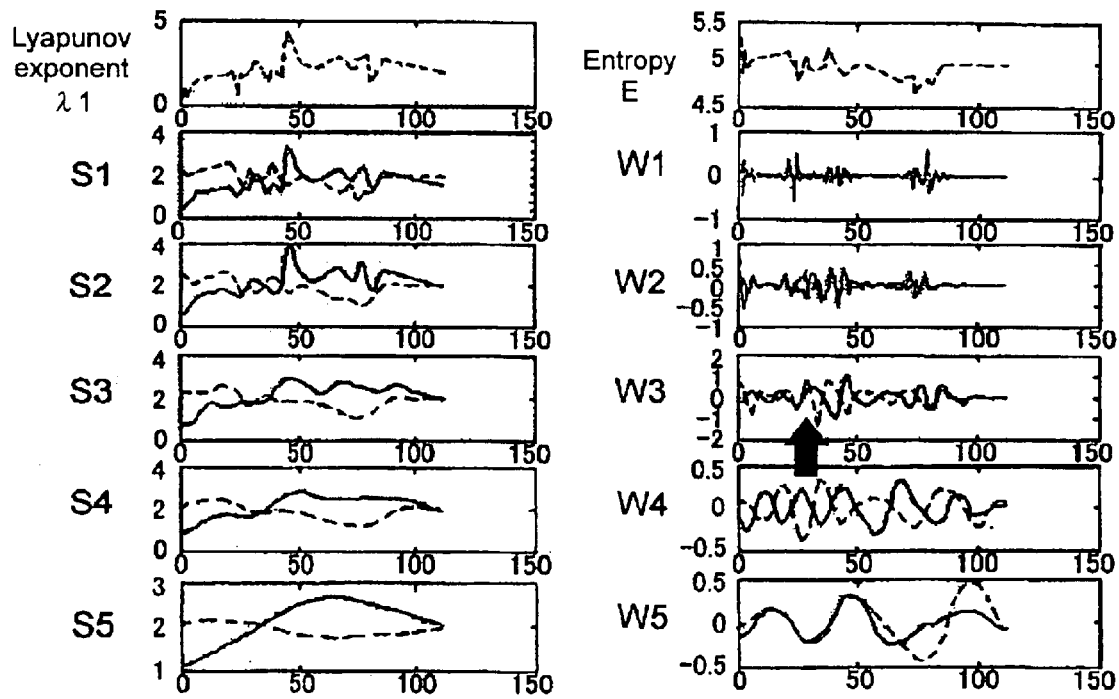
FIG. 19 shows graphs overlaying the scaling coefficients and wavelet coefficients calculated by Multiple Wavelet Resolution.
Figure 20:
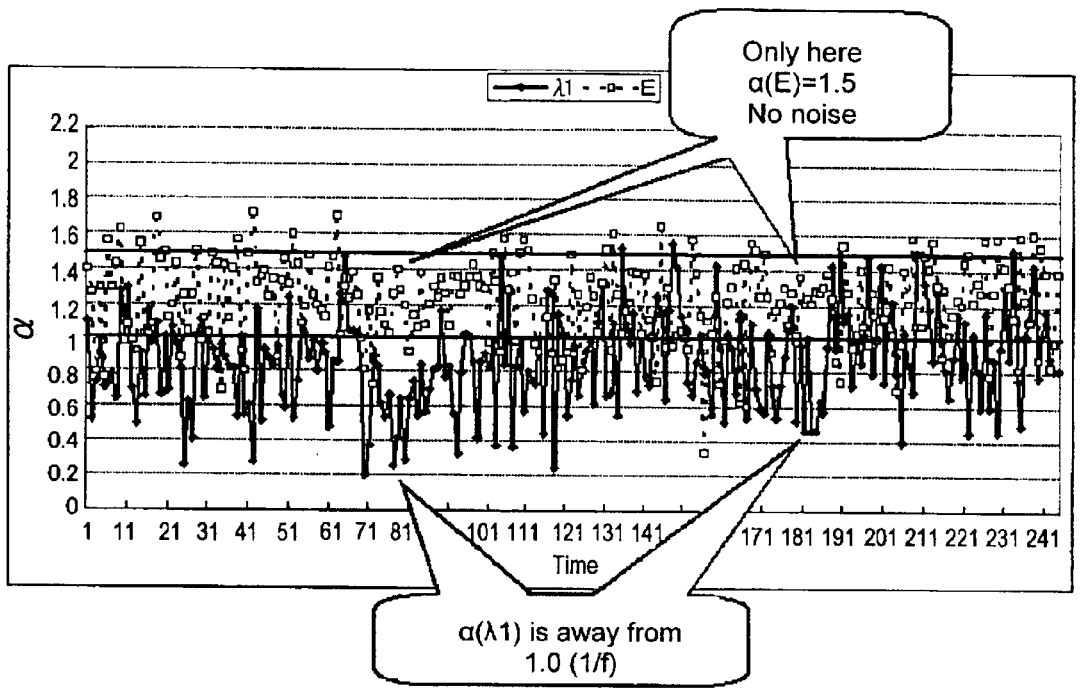
FIGS. 20 and 21 show results of microscopic DFA method and macroscopic DFA method in DFA method, respectively.
Figure 21:
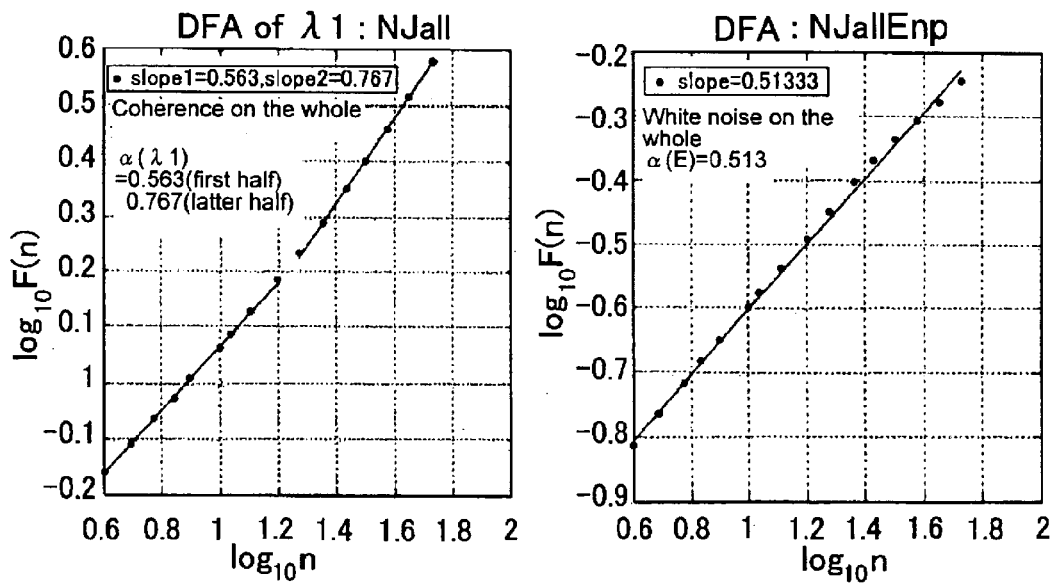

An example of judging a depressive Patient A (56-year-old male) is shown as the first example. This patient was diagnosed as having depression by a doctor and was prescribed Benzodiazepines Alplazolam (Solanax) 0.4 mg×3 and Bromazepan (Lendormin) 0.25 mg×1, antidepressants Maprotiline (Ludiomil) 25 mg×5, Amoxapine (Amoxapine) 25 mg×3 and Imipramine (Tofranil) 10 mg×6. The pulse wave of this patient was measured using the pulse wave collection system from Computer Convenience Inc. as described in the Japanese patent number 1891534, and the Multiple Wavelet Resolution of Lyapunov exponent and entropy was carried out to calculate the scaling coefficients and the wavelet coefficients according to the method of the second embodiment. The results are overlaid to prepare graphs as shown in FIG. 19, in which a critical point indicating the effect of medication is observed at the arrow. FIGS. 20 and 21 show the result of microscopic DFA method and macroscopic DFA method of the third embodiment, respectively. As shown in FIG. 21, the result of macroscopic DFA method of Lyapunov exponent, α, has a slope changing between the first half and the latter half. The value in the first half is 0.563 and the latter half is 0.767 approaching 1, showing that the condition of the patient ameliorates. Actually, the clinical symptom and subjective symptom of this patient were recovered completely.

EXAMPLE 2

Figure 22:
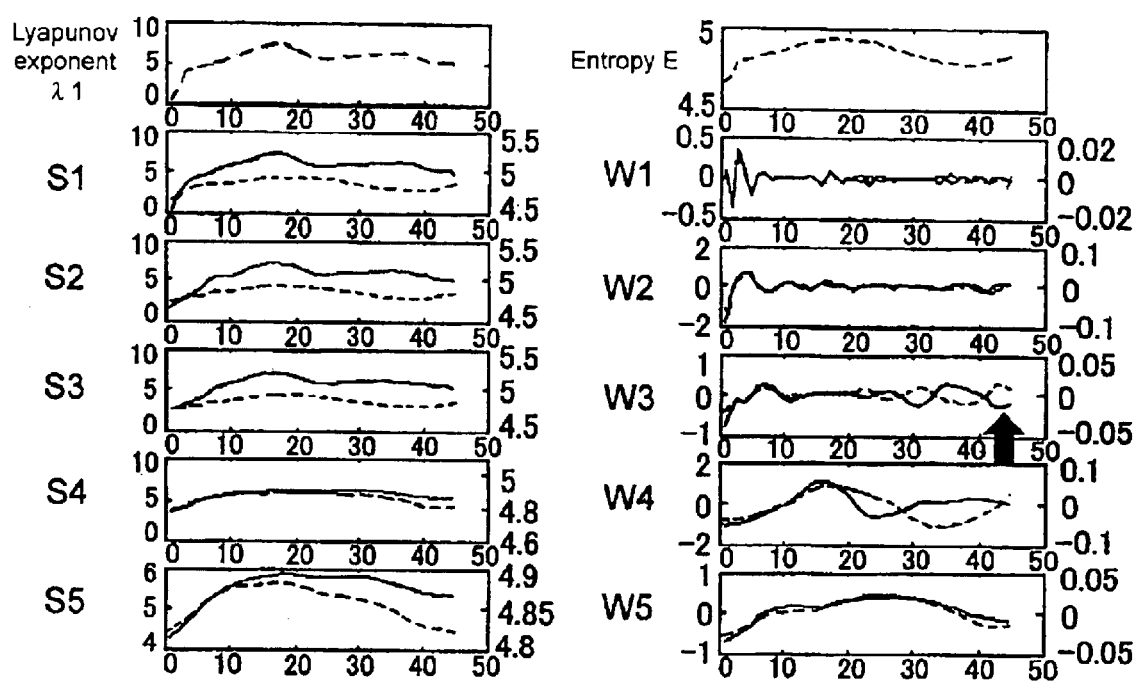
FIG. 22 show graphs overlaying scaling coefficients and wavelet coefficients calculated from the measurement data on Patient B by Multiple Wavelet Resolution of Lyapunov exponents and entropies using the method of the second embodiment.
Figure 23:
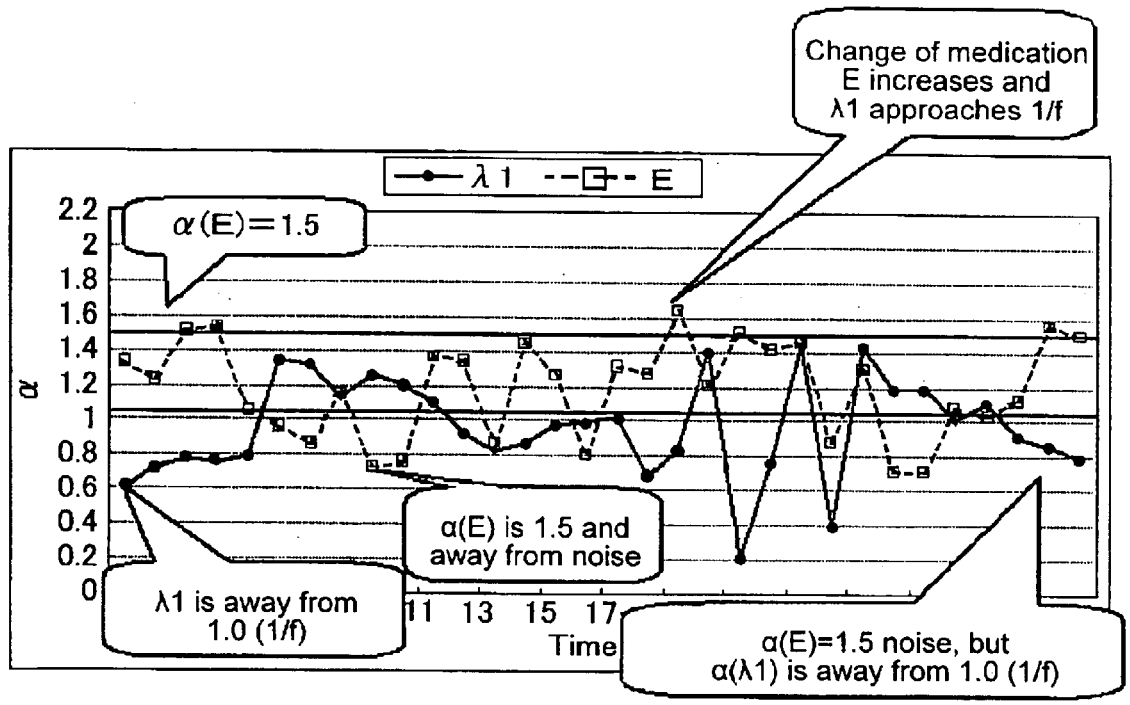
FIGS. 23 and 24 show results of microscopic DFA method and macroscopic DFA method according to the third embodiment, respectively.
Figure 24:
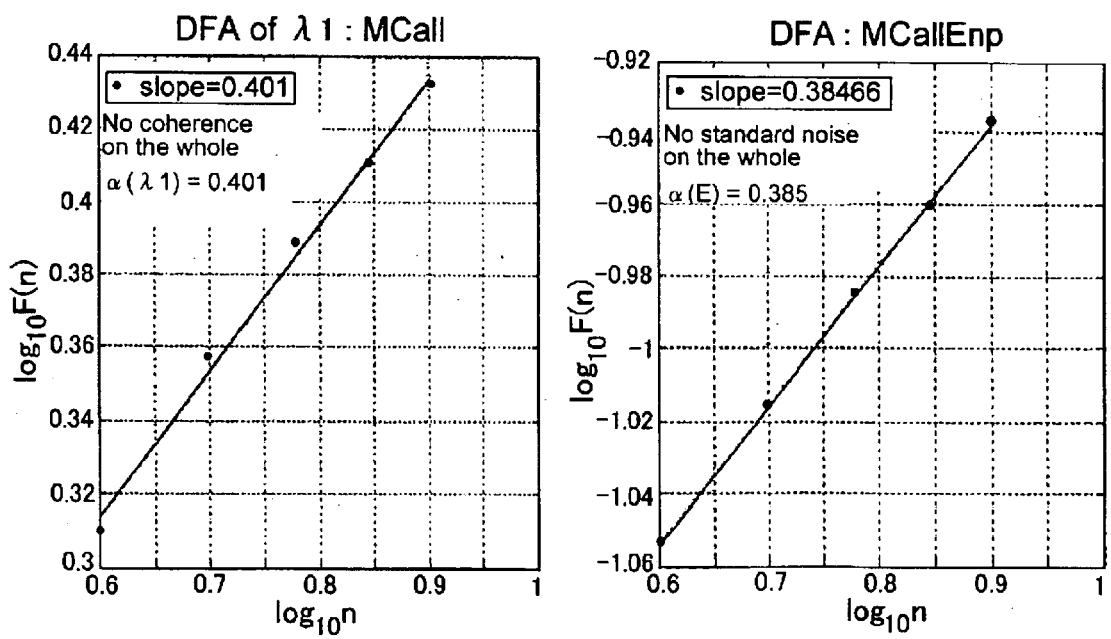

An example of judging another depressive Patient B (58-year-old male) is shown as the second example. FIG. 22 shows graphs overlaying the scaling coefficients and wavelet coefficients calculated from the measurement data on Patient B by Multiple Wavelet Resolution of Lyapunov exponent and entropy using the method of the second embodiment. FIGS. 23 and 24 show the results of microscopic DFA method and macroscopic DFA method of the third embodiment, respectively.

Since a mirror dynamics patterns in FIG. 22 are weak overall (only seen in the last part at the right end of the graph), it is judged that a quick recovery of the state would not be expected. In FIG. 24, the result of macroscopic DFA method of Lyapunov exponent and entropy, both αs are small values, therefore both the effect of medication and the condition of the patient are judged to be in a bad state. Actually, the clinical symptom and the subjective symptom were not recovered although Cloxazolam 1 mg and Amoxapine 25 mg×2 was administered to Patient B, and the change of clinical symptom was not observed even three months after this measurement.

It is clear from the above two examples: unlike the nonequilibrium open system of mere molecular association, a living body symmetrically changes the Lyapunov exponent and the entropy, i.e., the indices of chaotic nature, and this character serves as a barometer of the soundness of life. Accordingly, the clinical symptom of Patient B, who did not have this symmetrical variation in fluctuation, was not ameliorated even after several months, and the symptom of Patient A with such variation was completely cured after several months.

EXAMPLE 3

Figure 25:
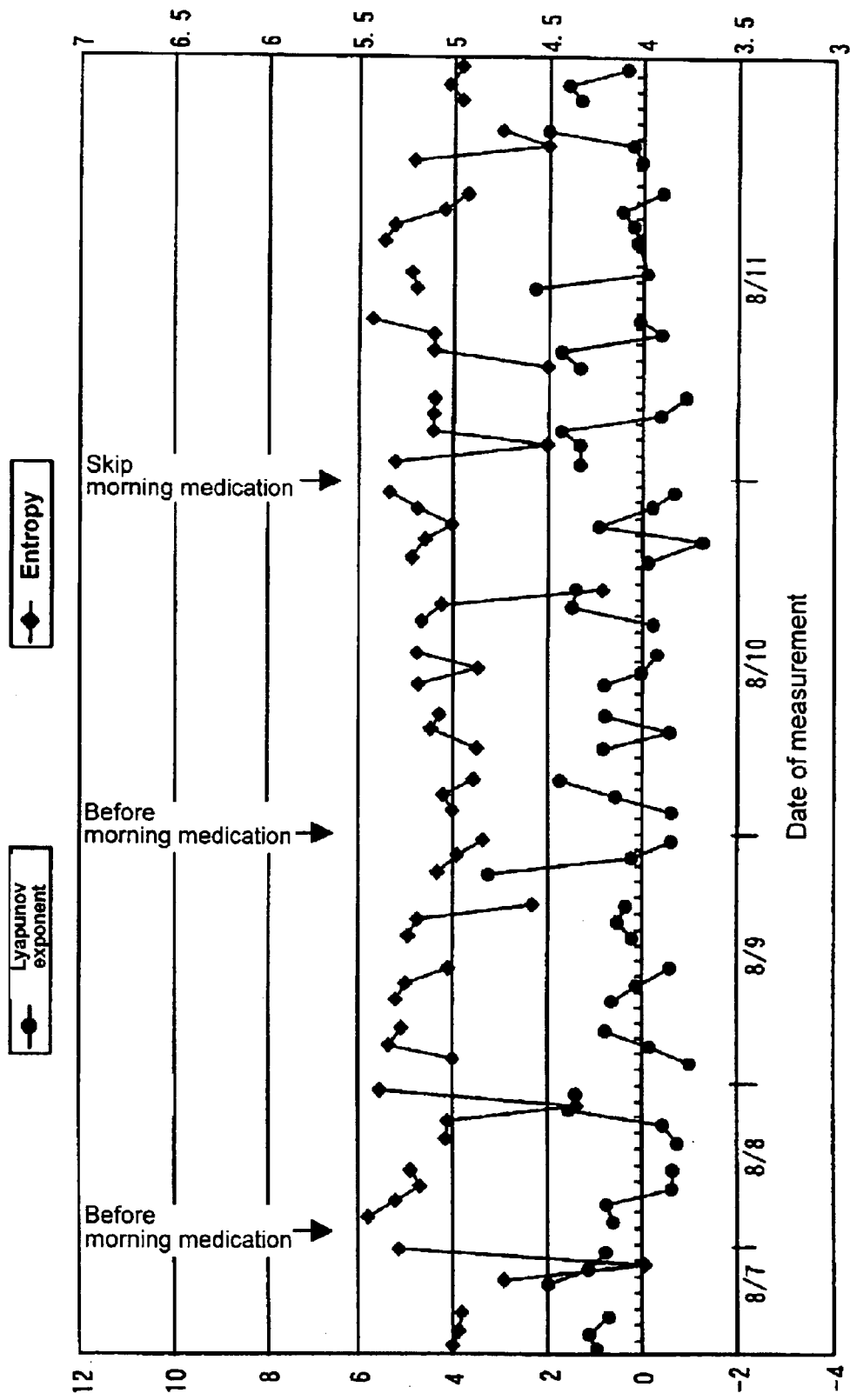
FIG. 25 shows the values of Lyapunov exponent and entropy of depressive Patient A during August 7–11th.

An example of judging the same depressive Patient A as in the first example (56-year-old male) is shown as the third example. The pulse wave of Patient A was measured in the same manner as in example 1 on August 7th, and the Lyapunov exponent was calculated. The values of three-times measurements at an interval of about 10 minutes were 0.98, 1.16 and 0.71, as shown in FIG. 25. The corresponding entropy values calculated according to the above-described method were 5.00, 4.96 and 4.95. When measured at 4 p.m., Lyapunov exponent values took 1.97, 1.15 and 0.76, and entropy values 4.72, 3.98 and 5.29. In FIG. 25 where the entropy and the Lyapunov exponent values are overlaid, as the results of four-times measurements started from 8:40 on August 8th, the entropy value at each time took 5.45, 5.30, 5.17 and 5.22 and the corresponding Lyapunov exponent values 0.59, 0.75, −0.62 and −0.64, showing an greatly increasing difference between the values of two types of indices. The difference gradually decreased from the morning toward evening on August 9th, while on August 10th the two indices varied with fluctuation in such a manner that the difference increased until the third measurement, decreased at the fourth and increased at the fifth. Focusing only on the Lyapunov exponent measured during August 7th to 11th, the dispersion in one measurement group is almost equal to the dispersion between each measurement group, and fluctuation can hardly be observed. Although worst is behind clinically, the state hardly showed a sign of improvement neither in a clinical symptom nor in a subjective symptom of the patient. However, while such dynamic variation of two indices continued for one to two months, the clinical symptom and the subjective symptom of Patient A were fully recovered as shown in example 1.

It is supported also from many clinical examples to be described hereafter that such dynamism is the sign of an improvement. Accordingly, it became clear that an observation of the dynamism of two types of indices, which cannot be recognized from only the variation of Lyapunov exponent, will result in the forecast for the short-term and long-term effects of drug.

Next, the sufficient degree of fluctuation will be illustrated by the comparison with the following Example 4.

EXAMPLE 4

Figure 26:
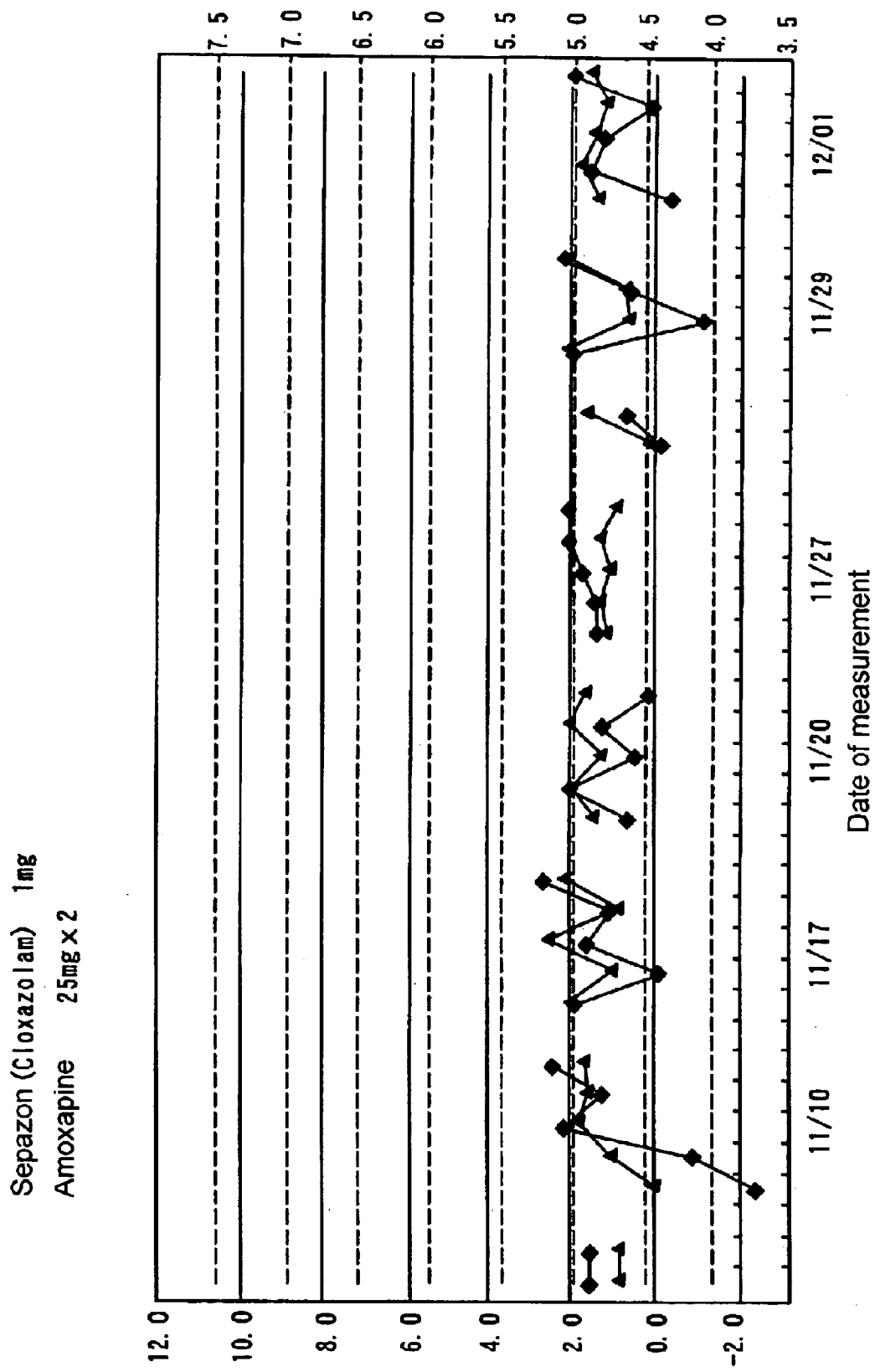
FIG. 26 indicates the values of Lyapunov exponent and entropy of depressive Patient B on November 10, 17, 20, 27, 29th and December 1st, under the condition of administration of Sepazon (Cloxazolam) 1 mg and Amoxapine 25 mg×2.

An example of judging the same depressive Patient B as in the second example (58-year-old male) is shown as the fourth example. During the measurement from November 10th to December 1st, the fluctuation can be barely observed as in FIG. 26. On November 10th, Lyapunov exponent took values −0.88, 0.25, 2.16, 1.27 and 2.49, and corresponding entropy values 4.20, 4.56, 5.05, 4.78 and 4.96. AS shown in FIG. 26, only the first group of two points among the groups of measurement values (2 to 5 times) shows difference in all points, and the difference value is about 0.25 in entropy value and about 1 in Lyapunov exponent value. However, there is no measurement group having overall difference during the measurement from November 10th to December 1st.

In contrast, in the case of Patient A, when measured values of August 7th and 8th are overlaid, difference values are about 1 in entropy value and about 4 in Lyapunov exponent. In comparison of two figures, apparent dynamic variation in FIG. 25 is indicated by the actual numbers as described above. Another judgement for a fluctuation depends on whether there is a directional property of variation with time. In this example, the directional property of variation in Patient A showed both increasing and decreasing directions between the measurement groups of 1 or 2 days, while in Patient B no such directional property was observed between the measurement groups, i.e. there was no fluctuation as in the same level as found in Patient A. As described above, the dose of drugs for Patient A was gradually decreased from September to October, and then both the judgement by the doctor and the subjective symptom of Patient A are fully recovered in October. The variations of two indices from October 2nd to 31st are shown in FIG. 27.

Figure 27:
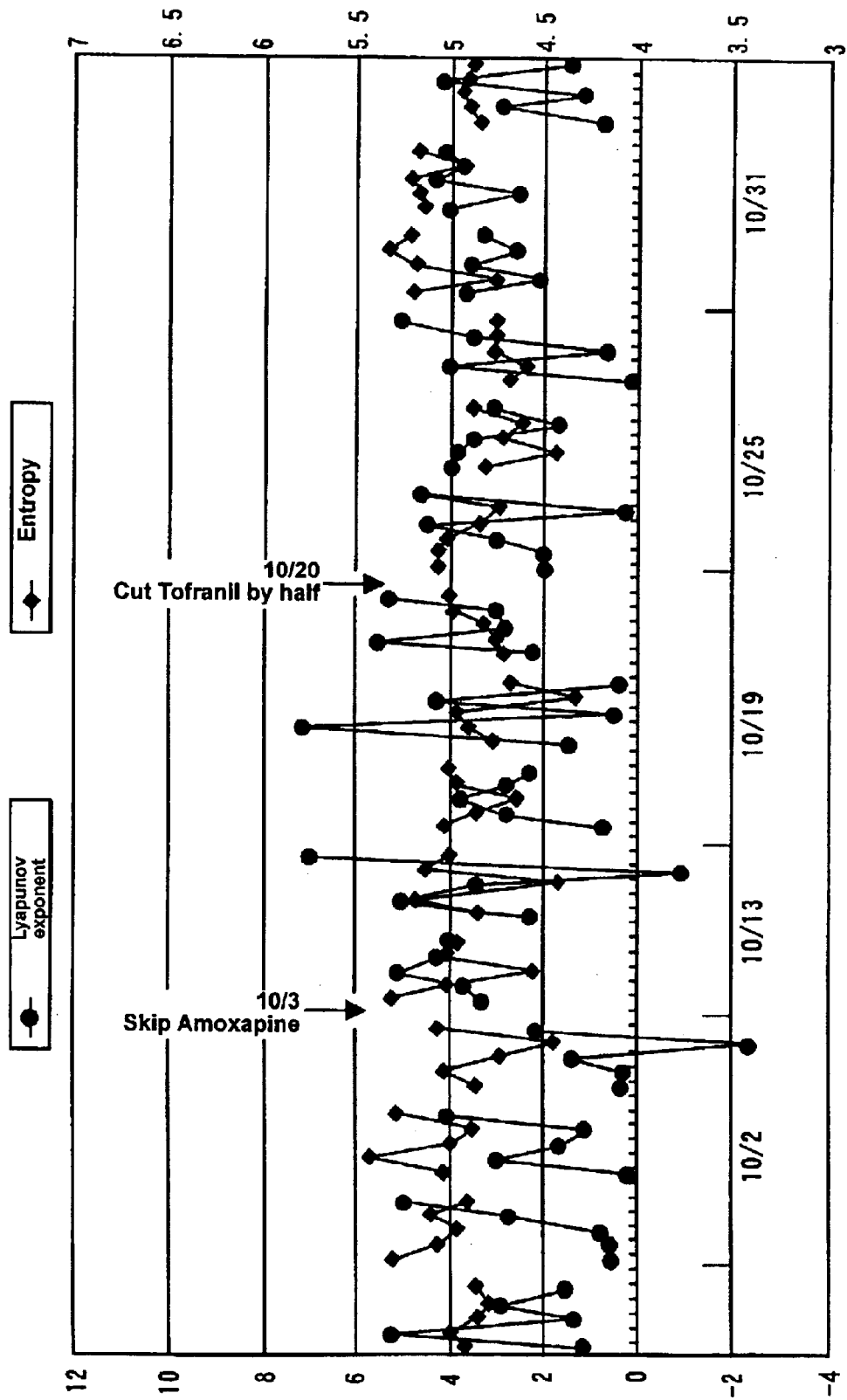
FIG. 27 indicates the values of Lyapunov exponent and entropy of Patient A on October 2nd, 13, 19, 25 and 31st.
Figure 28:
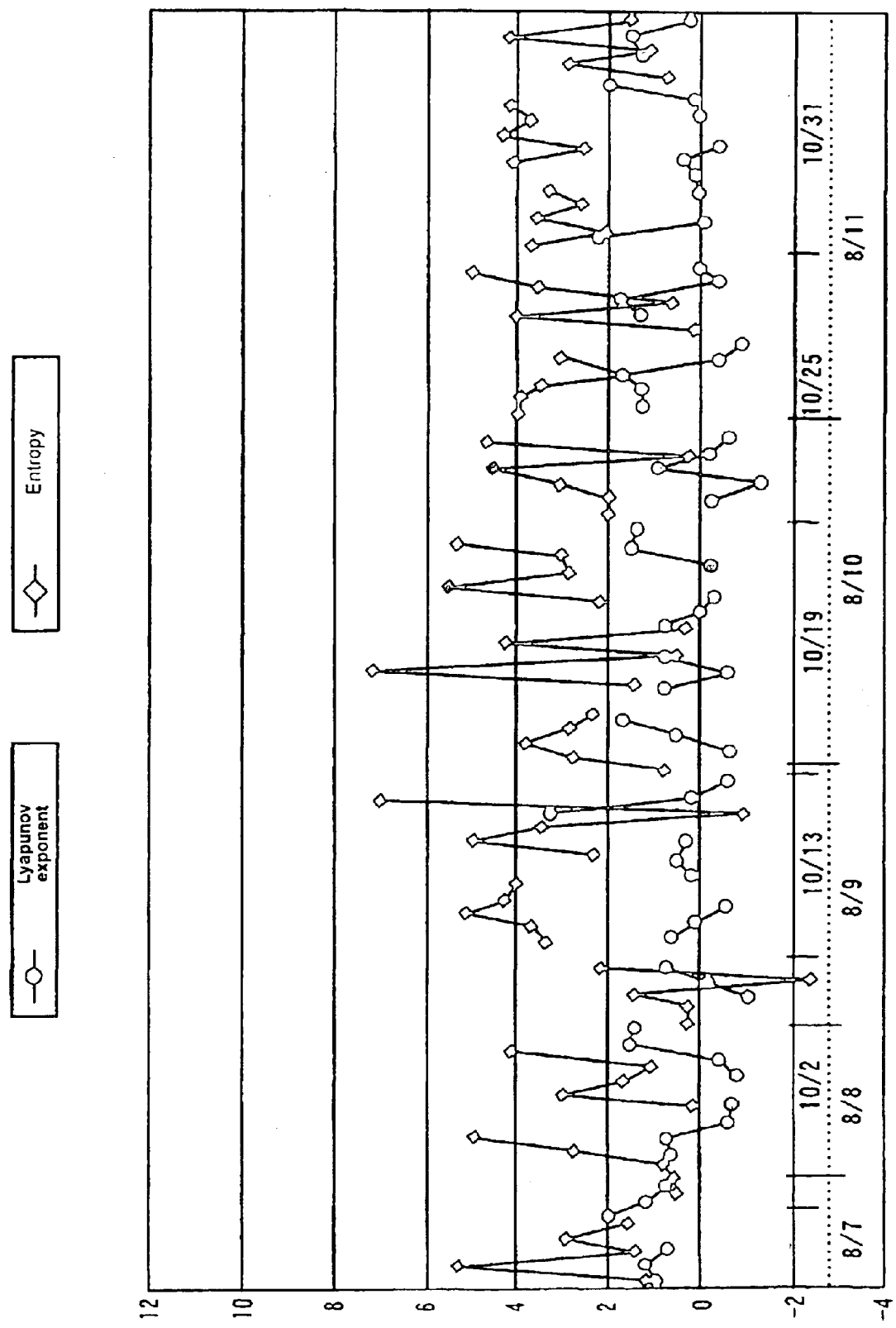
FIG. 28 shows Lyapunov exponent on August 7–11th (●) and Lyapunov exponent (♦) on October 2nd, 13, 19, 25 and 31st of Patient A.

In FIG. 28, the Lyapunov exponents of FIG. 25 (August 7th–11th) and FIG. 27 (October 2nd–31st) are compared. FIG. 25 has a variation in the range of 0 to 2, while FIG. 27 has a variation in the range of about 0 to 6 showing the rise of the Lyapunov exponent as an absolute value (average value). On the other hand, as to the entropy values in the same period, FIG. 25 has a variation in the range of about 4.5 to 5.5, while FIG. 27 has values that are generally lower than those in FIG. 25 in the same region. Patient B showed no changes in clinical symptom even three months after this measurement.

Similarly as in the first and second examples, it is also clear from the third and fourth examples: unlike the non-equilibrium open system of mere molecular association, a living body symmetrically changes the Lyapunov exponent and the entropy, i.e., the indices of chaotic nature, and this character serves as a barometer of the soundness of life.

It is clear from the above that the judgement about the effectiveness of a drug can be made based on the observation of the symmetric dynamism in Lyapunov exponent and entropy at the time of several hours to several days after medication or several dozen minutes after medication in the below example. If this dynamism is maintained, a long-term effect can also be judged as normalization of the absolute value of both indices.

Figure 29:
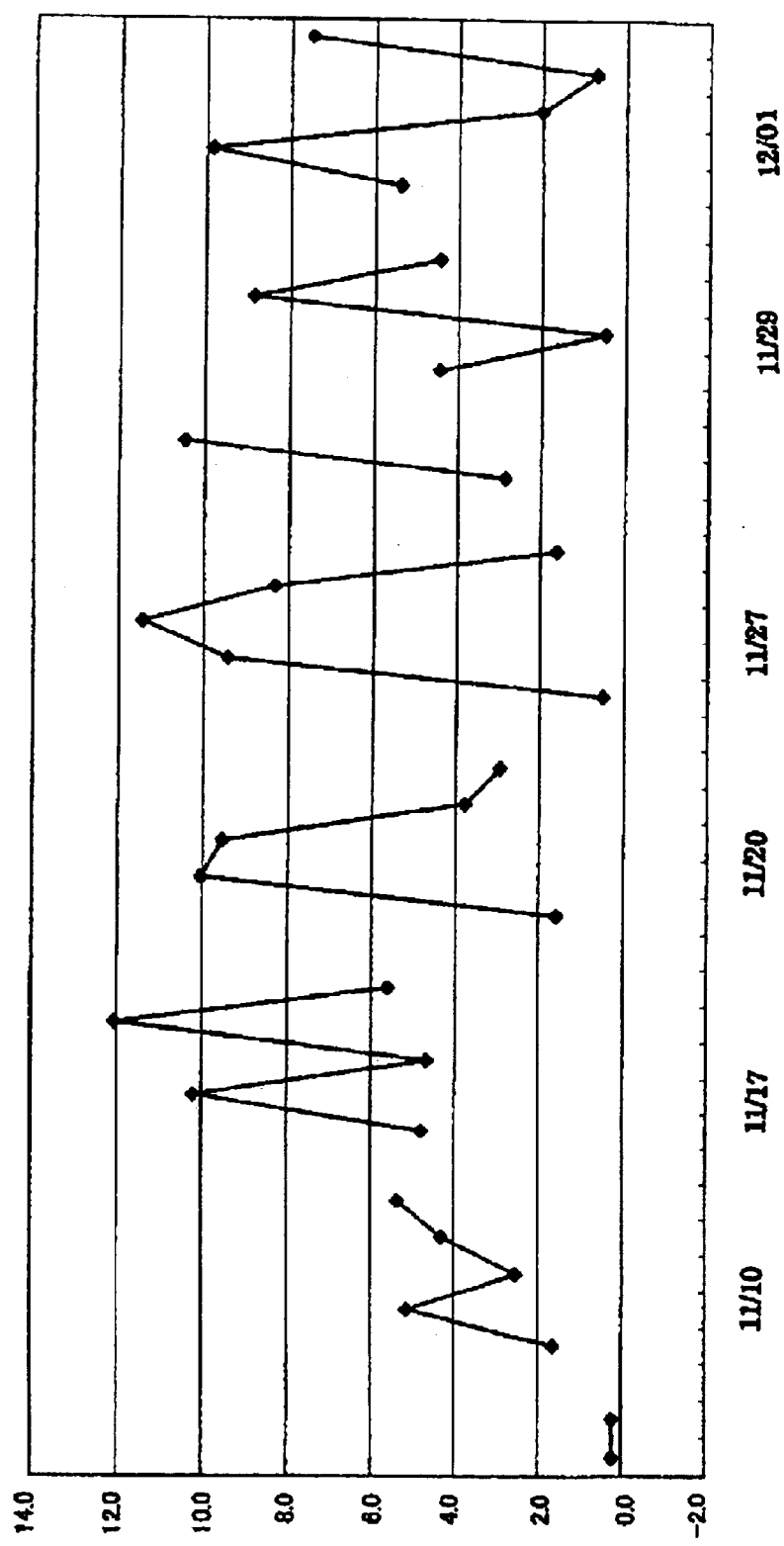
FIG. 29 indicates the Lyapunov exponent of Patient B before the application of a high-pass filter (1 Hz).
Figure 30:
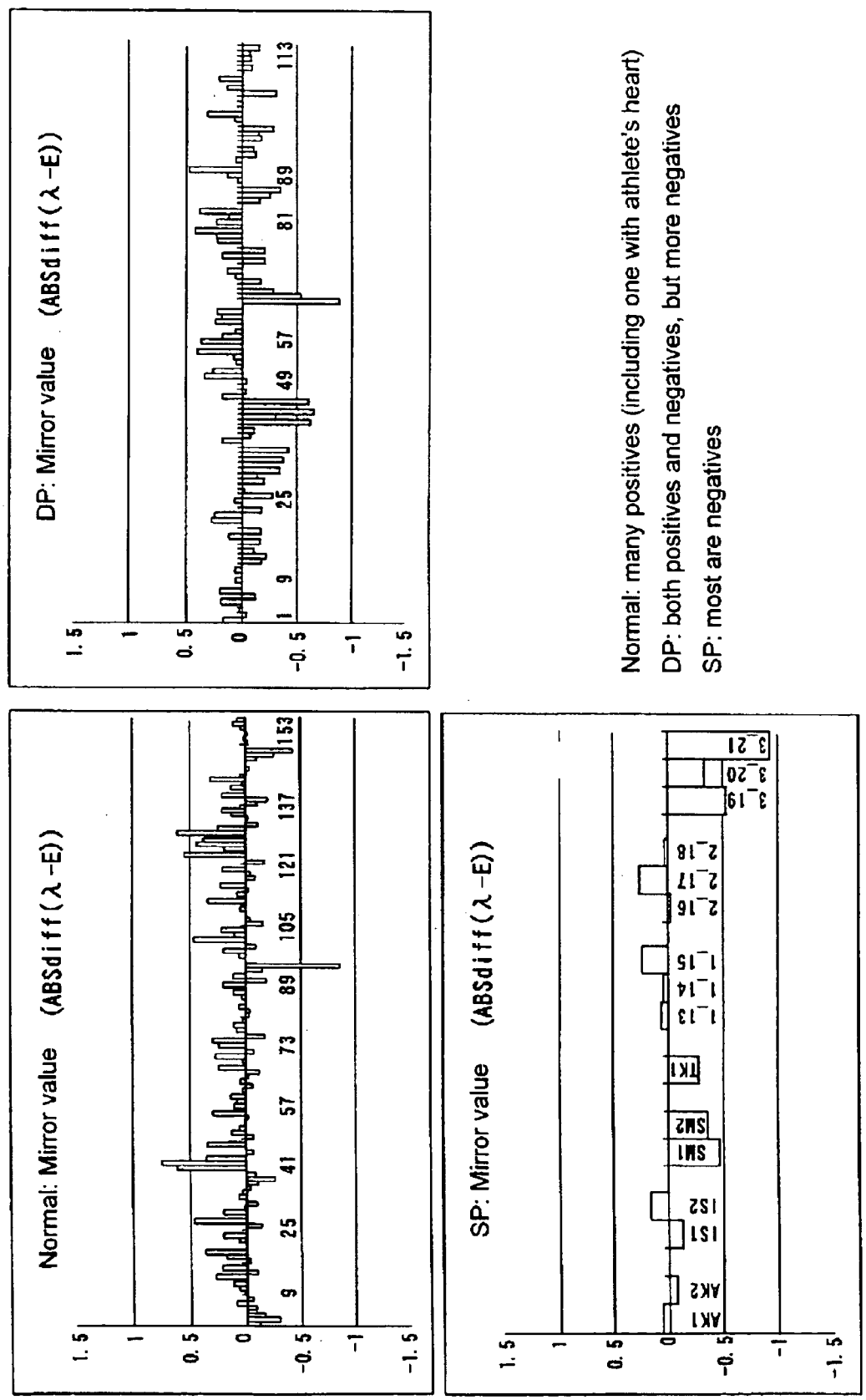
FIG. 30 is an example illustrating the analysis result of normality, DP (depression) and SP (schizophrenia) by Mirror value.

Apart from this, the Lyapunov exponent of the patient B shown in FIG. 29 is the value before being applied a high-pass filter (1 Hz; above-mentioned Chaos Theory Tamed, p153) for removing oscillation of a baseline and shows significant variation from near 0 to 10 or more in one measurement group. As to the magnitude of mere fluctuation, no greater variation beyond this can be supposed, and the margin of decline after applying the filter is extraordinarily great as compared with a normal value. This decreasing represents the abnormalities of this patient's chaotic nature, and indicates the schizophrenic disposition of this patient, contrary to the diagnosis by the doctor. On the other hand, this data shows that the fluctuation of only Lyapunov exponent cannot be used as an index of soundness. In terms of symmetric dynamism and improvement of absolute value, a filtered graph of Patient A is mostly in agreement with an unfiltered graph, showing that the state of Patient B can be accurately indicated by this decreasing.

Figure 15:
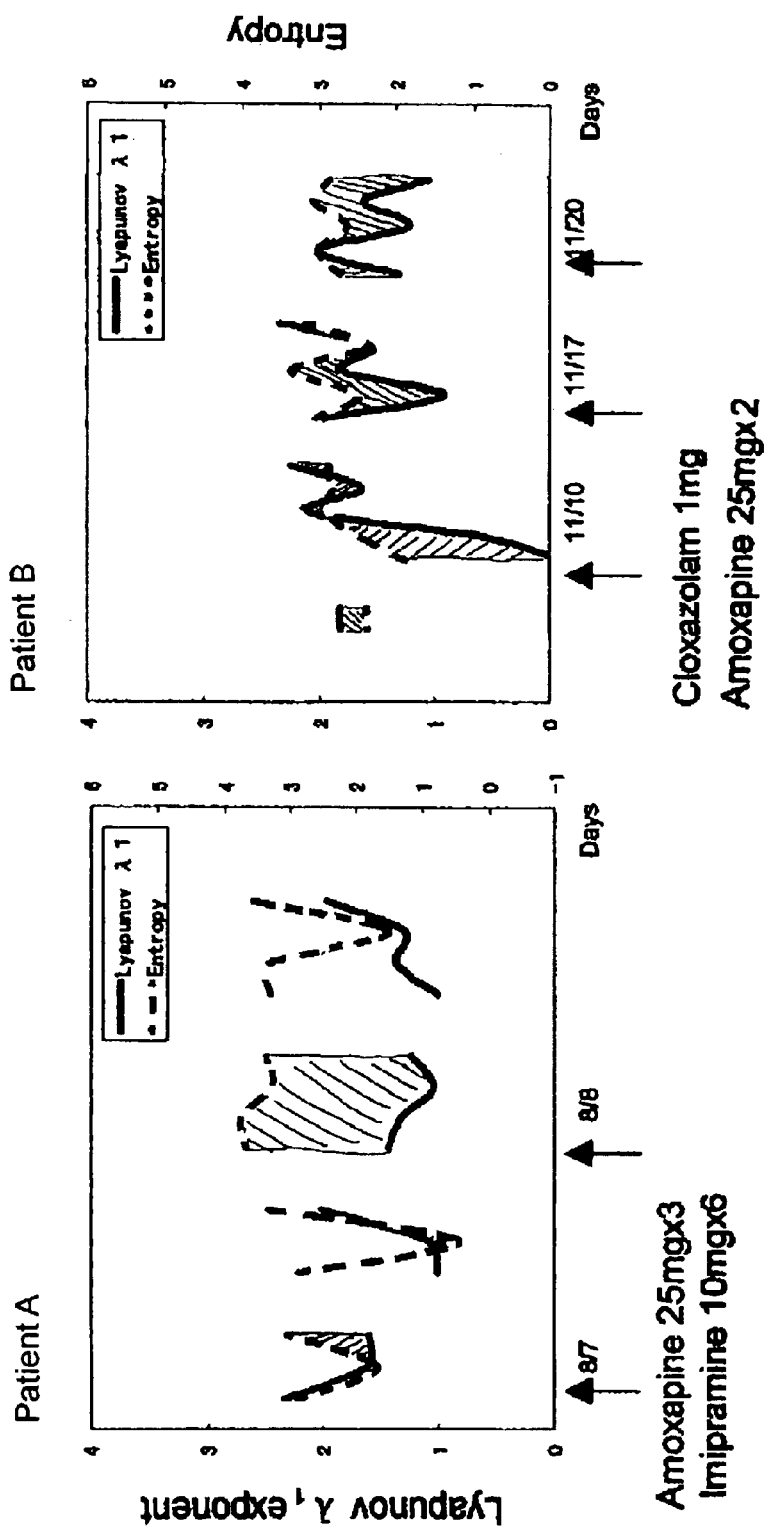
FIG. 15 shows time variations of entropy and Lyapunov exponent ($\lambda 1$) of Patient A and Patient B. The vertical axis indicates Lyapunov exponent and the horizontal axis measurement date.

FIG. 15 shows the transitions of variations of entropies and Lyapunov exponents ($\lambda 1$) of Patient A and Patient B. In Patient A, the difference (shadow area) between entropy and Lyapunov exponent ($\lambda 1$) is changed, showing that combined use of Amoxapine (25 mg×3) and Imipramine (10 mg×6) is effective. As to Patient B, the difference (shadow area) of entropy and Lyapunov exponent ($\lambda 1$) has a little change, showing that the medication of Cloxazolam (1 mg) and Amoxapine (25 mg×2) is not effective.

INDUSTRIAL APPLICABILITY

According to the present judging method for a biological state, mental or physical state of a subject living body such as human at the time of measurement, for example, whether diseased or not, a degree of disease, a degree of fatigue etc. can be judged accurately. Using the present judging method, a biological state is measured before and after drug medication, physical exercise, and externally stimulating action (music, noise, conversation, high or low temperature, humidity, light and darkness (illuminance), etc.), and then the influence of these actions on the biological state can be judged. Such judging method is useful for a diagnostic support system of disease by a doctor, choice of drugs, determination of medication schedule, early checkup of cancer or like diseases, etc.

In addition, when the judgement step is performed by an Artificial Neural Network, learning is carried out each time the reliable data as to a biological state is obtained to revise the internal state of an Artificial Neural Network, resulting in further improved judgement accuracy.

According to the method of the present invention, it can be judged whether a biological state is directed toward normal (improvement) or abnormal (deterioration). Therefore, it is effective for preventing or curing chronic diseases such as adult diseases, psychoneurosis such as depression (manic-depressive illness), schizophrenia or neurosis, and diseases or problematic behavior such as refusal to attend school or go to work (withdrawal), reducing the social cost accompanying deterioration of a biological state including medical expenses.

According to the present invention, the efficacy over an individual subject can be judged in the early stage of carrying out a therapeutic procedure, such as drug medication, dialysis, and use of medical implements. Accordingly, the effective therapeutic procedure can be chosen early, and the benefit of a patient and the reduction of medical cost can be provided.

By changing the population for calculating a judging criterion, the present invention can be adapted to judgements of various biological states, and therefore may be effectively used in various kinds of field. When carrying out the judgement of the same biological state, a judging criterion may change with countries, regions, ages, etc. However, the present invention is flexibly adaptable to this by changing a population for calculating a judging criterion.

Unlike the conventional method of using an average value of many data as a normal value, according to the present invention, the relative relation between an absolute value of specific data and other data is combined to enable tailor-made diagnosis that is unique to each person, and therefore the judgement of efficacy with a high degree of reliability can be attained.

What is claimed is:

1. A method of judging a biological state comprising using at least correlation or symmetry between Lyapunov exponent and entropy, wherein the Lyapunov exponent and entropy are indices that can express chaotic nature and are derived from time series data of biological signals from a subject, comprising:

the step of analyzing at least the correlation or the symmetry between the Lyapunov exponent and the entropy derived from time series data of biological signals from a subject; and the step of judging the biological state based on the result of analyzing at least the correlation or symmetry.

2. A method of judging a biological state using at least correlation between Lyapunov exponent and entropy,
   wherein the Lyapunov exponent and entropy are indices that can express chaotic nature and are derived from time series data of biological signals from a subject, wherein the correlation between the Lyapunov exponent and the entropy is analyzed using DFA method (Detrended Fluctuation Analysis).

3. A method of judging a biological state using at least correlation between Lyapunov exponent and entropy,
   wherein the Lyapunov exponent and entropy are indices that can express chaotic nature and are derived from time series data of biological signals from a subject, wherein the correlation between the Lyapunov exponent and the entropy is analyzed using the DFA method, which comprises the step of performing microscopic DFA analysis and the step of performing macroscopic DFA analysis.

4. A method of judging a biological state using at least symmetry between Lyapunov exponent and entropy,
   wherein the Lyapunov exponent and entropy are indices that can express chaotic nature and are derived from time series data of biological signals from a subject, wherein the correlation between the Lyapunov exponent and the entropy is analyzed using any method selected from the group consisting of M-symmetry method, Wavelet analysis method and a method based on Mirror value.

5. A method of judging a biological state using at least correlation or symmetry between Lyapunov exponent and entropy,
   wherein the Lyapunov exponent and entropy are indices that can express chaotic nature and are derived from time series data of biological signals from a subject, comprising the steps of:
   calculating two or more Lyapunov exponents and two or more entropies from time series data of biological signals from a subject and determining the maximum values among the Lyapunov exponents as a maximum Lyapunov exponents;
   determining offset values (Os) corresponding to the maximum Lyapunov exponents and the entropies;
   calculating Mirror values from the maximum Lyapunov exponents and the entropies; and
   calculating weighted Lyapunov exponents from the Mirror values and the offset values.

6. A method of judging a biological state using at least Higuchi fractal dimension,
   wherein Higuchi fractal dimension is an index that can express chaotic nature and is derived from time series data of biological signals from a subject, comprising using a ratio of two Higuchi fractal dimensions (D1/D2) or a F-constant as the Higuchi fractal dimension.

7. A method of judging a biological state using at least Higuchi fractal dimension,
   wherein Higuchi fractal dimension is an index that can express chaotic nature and is derived from time series data of biological signals from a subject, comprising the step of calculating a ratio of Higuchi fractal dimensions (D1/D2) by analyzing time series data of a biological signal from a subject using F-symmetry method, wherein the biological state is judged based on at least the ratio of Higuchi fractal dimensions (D1/D2).

8. A method of judging a biological state using:
   (1) correlation or symmetry between Lyapunov exponent and entropy; and
   (2) Higuchi fractal dimension,
   wherein the Lyapunov exponent, entropy and Higuchi fractal dimension are indices that can express chaotic nature and are derived from time series data of biological signals from a subject wherein the time series data of a biological signal are obtained from a pulse wave.

9. A method of judging efficacy of an action that may affect a biological state comprising the steps of:
   judging the biological state at a certain point of time according to at least correlation or symmetry between Lyapunov exponent and entropy,
   wherein the Lyapunov exponent and entropy are indices that can express chaotic nature and are derived from time series data of biological signals from a subject;
   taking the action that may change the biological state;
   analyzing time series data of biological signal after the action to determine correlation and/or symmetry between Lyapunov exponent and entropy; and
   comparing at least the correlation or the symmetry between Lyapunov exponent and entropy before the action with at least the correlation or the symmetry between Lyapunov exponent and entropy after the action to judge whether an influence of the action on a living body is positive, negative or neutral (unchanging).

10. The method according to claim 9, wherein the action is selected from the group consisting of preventive or therapeutic actions on diseases selected from medication, dialysis, radiation or laser irradiation, treatment by electric or magnetic pulse, rehabilitation, ingestion of food that may ameliorate a biological state, and producing a physical or mental stimulus.

11. A method of judging a biological state using at least correlation or symmetry between Lyapunov exponent and entropy,
    wherein the Lyapunov exponent and entropy are indices that can express chaotic nature and are derived from time series data of biological signals from a subject, comprising the steps of:
    calculating two or more Lyapunov exponents and two or more entropies from time series data of biological signals from a subject and determining the maximum values among the Lyapunov exponents as maximum Lyapunov exponents; and
    calculating scaling coefficients and wavelet coefficients from the maximum Lyapunov exponents and the entropies.

12. A method of judging a biological state using at least correlation or symmetry between Lyapunov exponent and entropy,
    wherein the Lyapunov exponent and entropy are indices that can express chaotic nature and are derived from time series data of biological signals from a subject, comprising judging a calculation result of time series data of biological signals from the subject using an Artificial Neural Network.

13. A system for judging a biological state comprising a measuring apparatus to collect time series data of biological signals from a subject and a judging apparatus for judging the biological state based on the time series data,
    wherein the measuring apparatus transmits the time series data via a communication line; and the judging apparatus calculates from the transmitted time series data at least correlation or symmetry between Lyapunov exponent and entropy as indices that can express chaotic nature, and uses the calculation result to perform a judgement, wherein the judging apparatus transmits a result of the judgement to the measuring apparatus.

14. A program for judging a biological state comprised in an apparatus for judging a biological state of a subject based on time series data of biological signals from the subject,
wherein a function of calculating at least correlation or symmetry between Lyapunov exponent and entropy as indices that can express chaotic nature from the time series data is fulfilled by the apparatus further fulfilling the functions of:
determining maximum values among the two or more Lyapunov exponents as maximum Lyapunov exponents;
determining offset values corresponding to the maximum Lyapunov exponents and the entropies;
calculating Mirror values from the maximum Lyapunov exponents and the entropies; and
calculating weighted Lyapunov exponents from the Mirror values and the offset values.

15. A program for judging a biological state comprised in an apparatus for judging a biological state of a subject based on time series data of biological signals from the subject,
wherein a function of calculating at least correlation or symmetry between Lyapunov exponent and entropy as indices that can express chaotic nature from the time series data is fulfilled by the apparatus further fulfilling the functions of:
determining maximum values among the two or more Lyapunov exponents as maximum Lyapunov exponents; and
calculating scaling coefficients and wavelet coefficients from the maximum Lyapunov exponents and the entropies.

16. A program for judging a biological state comprised in an apparatus for judging a biological state of a subject based on time series data of biological signals from the subject,
wherein a function of calculating at least correlation or symmetry between Lyapunov exponent and entropy as indices that can express chaotic nature from the time series data is fulfilled by the apparatus further fulfilling the function of performing macroscopic DFA method and microscopic DFA method with respect to the Lyapunov exponent and the entropy.

17. A program for judging a biological state comprised in an apparatus for judging a biological state of a subject based on time series data of biological signals from the subject,
wherein a function of calculating at least Higuchi fractal dimension as an index that can express chaotic nature from the time series data is fulfilled by the apparatus, fulfilling the function of calculating Higuchi fractal dimension and F-constant from the time series data.

18. A computer-readable recording medium holding the judging program according to any one of claims 14 to 17.

19. The method according to claim 6 comprising judging a calculation result of time series data of biological signals from the subject using an Artificial Neural Network.

20. A system for judging a biological state comprising a measuring apparatus to collect time series data of biological signals from a subject and a judging apparatus for judging the biological state based on the time series data,
wherein the measuring apparatus calculates from the transmitted time series data at least correlation or symmetry between Lyapunov exponent and entropy as indices that can express chaotic nature and transmits the calculation result via a communication line; and
the judging apparatus uses the calculation result to perform a judgement,
wherein the judging apparatus transmits a result of the judgement to the measuring apparatus.

* * * * *